United States Patent [19]

Yoo et al.

[11] Patent Number: 5,300,511
[45] Date of Patent: Apr. 5, 1994

[54] SPIRO-BENZOPYRAN DERIVATIVES AND USEFUL FOR TREATING ASTHMA AND HYPERTENSION

[75] Inventors: Sung-Eun Yoo; Kyu Y. Yi; Nak C. Jeong; Jee H. Suh; Seon-Ju Kim; Hwa-Sup Shin; Byung H. Lee; Kyu S. Jung, all of Daejeon, Rep. of Korea

[73] Assignee: Korea Research Institute of Chemical Technology, Daejeon, Rep. of Korea

[21] Appl. No.: 887,189

[22] Filed: May 21, 1992

[30] Foreign Application Priority Data

May 22, 1991 [KR] Rep. of Korea ............... 91-8244
May 30, 1991 [KR] Rep. of Korea ............... 91-8915
Dec. 26, 1991 [KR] Rep. of Korea ............... 91-24353

[51] Int. Cl.$^5$ ............... C07D 471/10; C07D 405/04; A61K 31/44
[52] U.S. Cl. ............... 514/278; 546/17; 546/18
[58] Field of Search ............... 546/17, 18; 514/278

[56] References Cited

U.S. PATENT DOCUMENTS 4,578,410 3/1986 Takahashi et al. ............... 524/102

*Primary Examiner*—Alan L. Rotman
*Attorney, Agent, or Firm*—Thomas J. Dodd; James D. Hall

[57] ABSTRACT

The present invention relates to novel benzopyran derivatives of formula(I) which have exellent effectiveness in the treatment of asthma as well as hypertension.

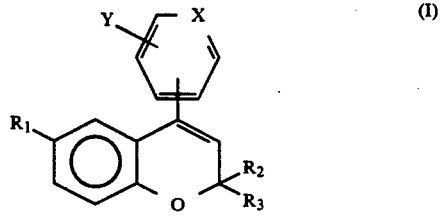

wherein
$R_1$ is —CN, —NO$_2$, —OCX$_1$X$_2$X$_3$, —NH$_2$, —NHSO$_2$R$^A$,

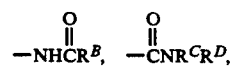

—SO$_2$R$^C$ or —SO$_2$NR$^C$R$^D$ wherein $X_1$, $X_2$ and $X_3$ are, each independently, F, Cl or H, except for that $X_1$, $X_2$ and $X_3$ may not be hydrogen atom simulaneously; $R^A$ and $R^B$ are, each independently, a hydrogen atom, or a C$_{1-6}$ alkyl group or an optionally substituted phenyl group with a halogen atom, or a straight or branched C$_{1-3}$ alkyl group; and $R^C$ and $R^D$ are, each independently, a hydrogen atom or a C$_{1-6}$ alkyl group or an optionally substituted phenyl group with a halogen atom, or a straight or branched C$_{1-3}$ alkyl group;
$R_2$ is a C$_{1-4}$ straight or branched alkyl group;
$R_3$ is a C$_{1-4}$ straight or branched alkyl group,

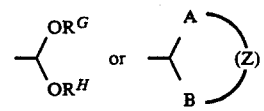

wherein R$^G$ and R$^H$ are, each independently, a C$_{1-6}$ alkyl group or optionally substituted phenyl group with a halogen atom, or a straight or branched C$_{1-3}$ alkyl group, A and B are, each independently, S or O; and Z is a C$_{1-3}$ straight or branched alkyl group; X is N or N→O.

5 Claims, No Drawings

SPIRO-BENZOPYRAN DERIVATIVES AND USEFUL FOR TREATING ASTHMA AND HYPERTENSION

FIELD OF THE INVENTION

The present invention relates to novel benzopyran derivatives which have excellent effectiveness in the treatment of hypertension by lowering blood pressure with a relaxation activity on vascular smooth muscle and, further, in the treatment of asthma by relaxing respiratory smooth muscle. The present invention also relates to processes for preparing such compounds; and to pharmaceutical compositions containing such compounds as an active ingredient.

BACKGROUND OF THE INVENTION

Hitherto, it has been known that a number of compounds which have relaxation activity on vascular smooth muscle by inhibiting influx of calcium ions into cells are useful in the treatment of diseases in cardiac circulatory. As such compounds, for example, calcium channel inhibitors and sodium channel inhibitors have been already developed, and, further, many studies on potassium channel activators have been made. Examples of such potassium channel activators include Pinacidil used frequently as a capillary vasodilator drug; Nicorandil used as an anti-stenocardia drug; and Cromakalim of Beecham Group plc used as an antihypertensive agent.

European Patent Publication No. 093,535 filed by Beecham Group, plc. in the title of "novel chromene and chroman" discloses benzopyran derivatives of formula(A) and salts thereof:

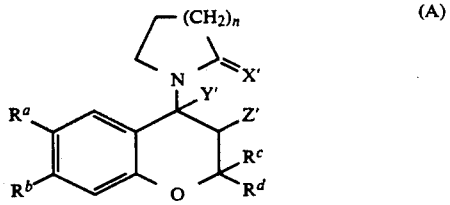

wherein:
one of $R^a$ and $R^b$ is a hydrogen atom and the other is selected from the group consisting of a $C_{1-6}$ alkyl- and alkoxycarbonyl, $C_{1-6}$ alkyl-carbonyloxy, $C_{1-6}$ alkylhydroxymethyl, nitro, cyano, chloro, trifluoromethyl, $C_{1-6}$ alkyl- and alkoxysulfinyl, $C_{1-6}$ alkyl- and alkoxysulfonyl, $C_{1-6}$ alkyl- and alkoxycarbonylamino, $C_{1-6}$ alkyl- and alkoxysulfinylamino, $C_{1-6}$ alkyl- and alkoxysulfonylamino, $C_{1-6}$ alkyl- and alkoxythicarbonyl, $C_{1-6}$ alkyl- and alkoxythiocarbonyloxy, $C_{1-6}$ alkylthiomethyl, formyl, an optionally substituted aminosulfinyl, aminosulfonyl or aminocarbonyl, or a terminal substituted ethylenyl, —C($C_{1-6}$ alkyl) NOH, or —C($C_{1-6}$ alkyl)NNH$_2$ group; or
one of $R^a$ and $R^b$ is nitro, cyano or a $C_{1-6}$ alkylcarbonyl group and the other is methoxy or an optionally substituted amino group;
one of $R^c$ and $R^d$ is a hydrogen atom or a $C_{1-4}$ alkyl, and the other is a $C_{1-4}$ alkyl group; or
$R^c$ and $R^d$ together form a $C_{2-5}$ polymethylene;
X' is an oxygen or sulfur atom;
Y' and Z' are hydrogen atoms or together form a single bond; and n is 1 or 2.

Further, European Patent Publication No. 298,452 A2 filed by F. Hoffmann La Roche & Co. discloses benzopyran derivatives of formula(B) and pharmaceutical compositions containing same:

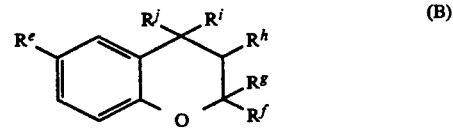

wherein:
$R^e$ is a hydrogen or halogen atom, or a trifluoromethyl, nitro, cyano, a lower alkyl, alkoxycarbonyl, alkylthio, alkylsulfonyl, alkanoyl, carbamoyl or mono- or di(lower alkyl) carbamoyl group;
$R^f$ is a hydrogen atom, lower alkyl or phenyl group;
$R^g$ is a hydrogen atom or lower alkyl group;
$R^h$ is a hydrogen atom or a hydroxy group; and, $R^i$ is a hydrogen atom; or $R^h$ and $R^i$ together form a C—C bond; and
$R^j$ is an aryl- or N-heteroaryl group whose 2-position is a hydroxy group, or, an N-oxide group in case of N-heteroaryl group.

Korean Patent Application No. 91-4602 filed by Merck Patent Gesellschaft mit beschrankter Haftung discloses a chromane derivative of formula(C) and a salt thereof:

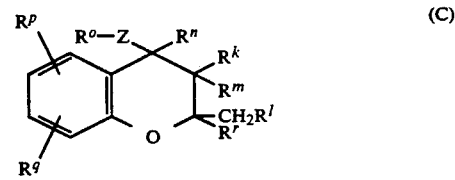

wherein
$R^k$ is H or A;
$R^l$ is F, Cl, Br, I, OH, OA, OAc, SA, $NO_2$, $NH_2$, NHA, $NA_2$, CH or COOA;
$R^m$ is H, OH, OA or OAc and $R^n$ is H; or $R^m$ and $R^n$ together form a single bond;
$R^O$ is an optionally mono- or di-substituted pyridyl, pyridazinyl, pyrimidinyl, pyrazinyl, oxohydropyridyl, oxodihydropyridyl, oxodihydropyridazinyl, oxodihydropyrimidinyl, oxodihydropyrazinyl, 2-pyrrolidinon-1-yl or 3-oxocyclopenten-1-yl with A, F, Cl, Br, I, OH, OA, OAc, SH, $NO_2$, $NH_2$, NHAc, COOH and/or COOA;
$R^p$ and $R^q$ are each independently H, A, HO, AO, CHO, ACO, ACS, HOOC, AOOC, AO—CS, ACOO, A—CS—O, hydroxyalkyl, mercaptoalkyl, $NO_2$, $NH_2$, NHA, $NA_2$, CN, F, Cl, Br, I, $CF_3$, ASO, $ASO_2$, AO—SO, AO—$SO_2$, ACNH, AO—CO—NH, $N_2HSO$, HANSO, $A_2NSO$, $H_2NSO_2$, $HANSO_2$, $A_2NSO_2$, $H_2NCO$, HANCO, $A_2NCO$, $A_2NCS$, HANCS, $A_2NCS$, ASONH, $ASO_2NH$, ASO—ONH, $AOSO_2NH$, ACO-alkyl, nitroalkyl, cyanoalkyl, A—C(=NOH) or A—C=(NNH$_2$);
$R^r$ is H or A;
Z is O, S, NH or a single bond;
A represents a $C_{1-6}$ alkyl group;
-alkyl represents a $C_{1-6}$ alkylene; and
Ac represents a $C_{1-8}$ alkanoyl or $C_{7-11}$ aroyl group.
The above compounds have been reported to be useful in the treatment of hypertension. However, another use of the compounds was reported in such references as Br. J. Pharmacol. 89, 395–405(1986), Br. J. Pharmacol. 165, 231–239(1989), and Br. J. Pharmacol. 95, 765–770(1988): i.e., the compounds may be used as a bronchodilator in addition to a blood pressure-lowering agent, since they relax smooth muscle by enhancing the hyperpolarization of the plasma membrane of a cell.

It has now been found that a novel class of benzopyrans have superior effectiveness in the treatment of both hypertension and asthma.

SUMMARY OF THE INVENTION

Accordingly, the present invention primarily pertains to novel benzopyran derivatives having excellent effectiveness in the treatment of both hypertension and asthma. Further, the present invention relates to processes for preparing such compounds; and to pharmaceutical compositions containing such compounds as an active ingredient.

DETAILED DESCRIPTION OF THE INVENTION

The present invention provides novel benzopyran derivatives of formula

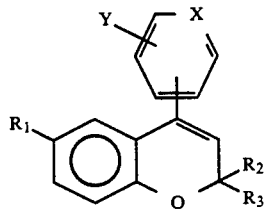

(I)

wherein
$R_1$ is —CN, —NO$_2$, —OCX$_1$X$_2$X$_3$, —NH$_2$, —NHSO$_2$R$^A$,

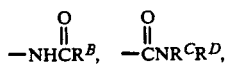

SO$_2$R$^C$ or —SO$_2$NR$^C$R$^D$ wherein X$_2$, X$_2$ and X$_3$ are, each independently, F, Cl or H, except that X$_1$, X$_2$ and X$_3$ may not be a hydrogen simultaneously; R$^A$ and R$^B$ are, each independently, a hydrogen atom, or a C$_{1-6}$ alkyl group or an optionally substituted phenyl group with a halogen atom, or a straight or branched C$_{1-3}$ alkyl group; and R$^C$ and R$^D$ are, each independently, a hydrogen atom or a C$_{1-6}$ alkyl group or an optionally substituted phenyl group with a halogen atom, or a straight or branched C$_{1-3}$ alkyl group;
$R_2$ is a C$_{1-4}$ straight or branched alkyl group;
$R_3$ is a C$_{1-4}$ straight or branched alkyl group,

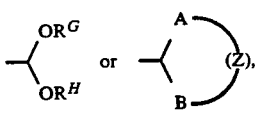

wherein R$^G$ and R$^H$ are, each independently, a C$_{1-6}$ alkyl group or an optionally substituted phenyl group with a halogen atom, or a straight or branched C$_{1-3}$ alkyl group; A and B are, each independently, S or O; and Z is a C$_{1-3}$ straight or branched alkyl group;

X is N or N→O, provided, however, when X is in 2-position,

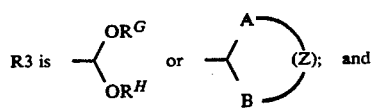

Y is a hydrogen or halogen atom, or an amino, hydroxy, lower alkoxy or lower alkyl group.

Preferred benzopyran derivatives of the present invention are the compounds of formula(I) wherein:
$R_1$ is —CN or —NO$_2$;
$R_2$ is a methyl group;
$R_3$ is a methyl group,

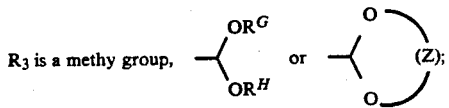

X is N→O, provided, however, when X is in 2-position, R$_3$ is not a methyl group; and
Y is H.

More preferred benzopyran derivatives of the present invention are the compounds of formula(1) wherein:
$R_1$ is —CN or —NO$_2$;
$R_2$ is a methyl group;
$R_3$ is a methyl group,

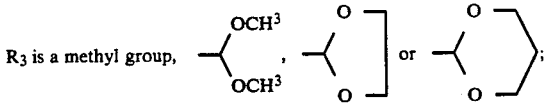

X is N→O, provided, however, when X is in 2-position, R$_3$ is not a methyl group; and
Y is H.

The novel benzopyran compounds of formula(I) may be present in the form of a racemic mixture of optically active isomers of formulae(I') and (I'') when R$_2$ and R$_3$ are different. Each of the isomers may be obtained separately which are also within the scope of the invention. Accordingly, the compounds of formula(I) include both isomers of formulae(I') and (I'') as well as the racemic mixture thereof:

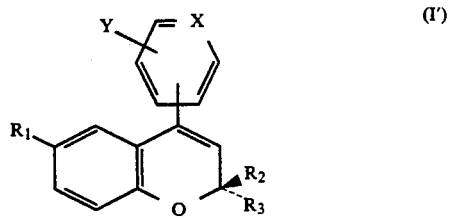

(I')

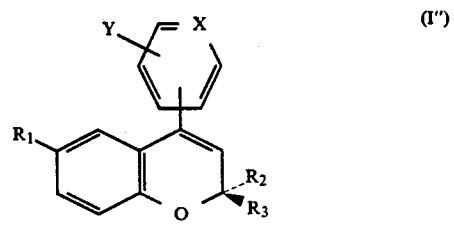

(I'')

wherein $R_1$, $R_2$, $R_3$, X and Y have the same meanings as defined above.

The present invention also provides processes for preparing the compounds of formula(i).

The benzopyran derivatives having the formula(1) according to the present invention may be prepared by a known method, for example, taught in EP 298452 A2, of which details are not disclosed herein.

The compounds of the present invention may also be prepared by employing a novel process shown in the following Reaction Scheme(1):

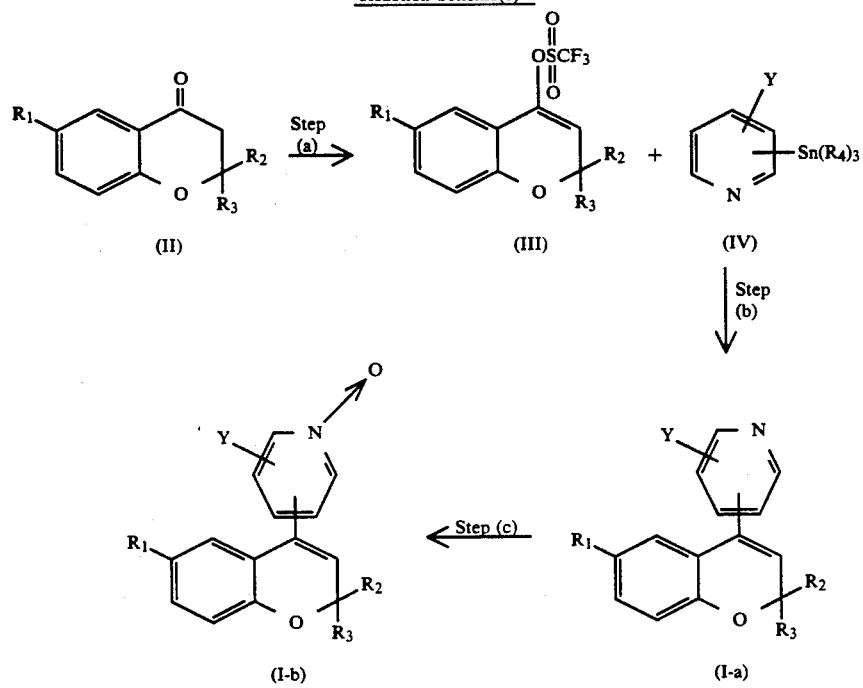

wherein $R_1$, $R_2$, $R_3$ and Y have the same meanings defined above; and $R_4$ is a $C_{1-4}$ alkyl group.

In the above process, Step(a) may be conducted by reacting a ketone derivative of formula(II) with anhydrous trifluorosulfonic acid and a tertiary amine in a solvent such as dichloromethane and chloroform at a temperature ranging from 0° C. to a room temperature; or, alternatively, converting the ketone derivative of formula(II) to an enolate by using a base such as lithium diisopropyl amine, lithium dihexamethylsilazamide, etc. and then reacting the enolate with N-phenyltrifluoromethane sulfonimide($Tf_2NPh$) in a solvent such as tetrahydrofuran(THF), ethers, THF-hexamethylphosphoric triamide (HMPA) or THF-tetramethyl ethylene diamine(TMEDA) at a temperature ranging from −78° C. to 0° C. under argon or nitrogen atomspheric environment to provide a vinyl triflate of formula(III).

Thereafter, Step(b) may be conducted by reacting the vinyl triflate of formula(III) with a trialkyltin derivative of formula(IV) in the presence of a catalyst to provide a benzopyran derivative of formula(I-a). Step(b) may be carried out in a solvent such as THF, N-methyl pyrrolidone(NMP) and dimethylformamide(DMF) in the presence of a catalytic mixture of a first component selected from the group consisting of tetrakis triphenyl-phosphine palladium, bisbenzylidine acetone palladium and dipalladium trisdibenzylidine acetone chloroform and a second component selected from the group consisting of triphenylphosphine, tri-2-furanylphosphine and triphenyl arsenic and using a chloride compound such as lithium chloride and sodium chloride at a temperature ranging from a room temperature to 70° C.; or alternatively, in a solvent such as THF in the presence of a catalytic mixture of palladium acetate and any one of triphenylphosphine, tri-2-furanylphosphine, trialkylamine a-nd triphenyl arsenic at the boiling point of the solvent employed.

Subsequently, Step(c) may be conducted by oxidizing the compound of formula(I-a) in the presence of an oxidizing agent to provide a benzopyran derivative of formula(I-b) of the present invention. The oxidizing agent includes m-chloroperbenzoic acid, hydrogen peroxide, dimethyldioxiran, oxon, etc; and, dichloromethane, chloroform, acetone or dioxane-water can be used as a reaction solvent. The reaction temperature may range from 0° C. to a room temperature.

Particularly, a compound of formula(I-c) may be further reacted to produce a compound of formula(I-d) or (I-e) by a process shown in the following Reaction Scheme(2):

Reaction Scheme(2)

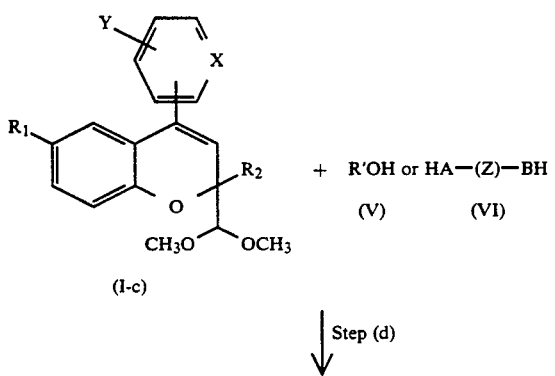

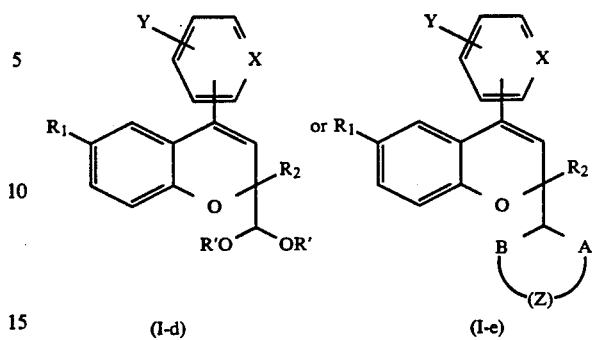

wherein $R_1$, $R_2$, A, B, X, Y and Z have the same meanings as defined above; and R' is a $C_{2-6}$ alkyl group or an optionally substituted phenyl group.

In the above process, Step(d) may be conducted by transacetallization of a compound of formula(I-c) with an excess amount of an alcohol of formula(V) or a diol or mercaptoalcohol of formula(VI) to provide a compound of formula(I-d) or (I-e), respectively. An acid catalyst may be usd in a catalytic amount; and examples of such acid catalyst include a conventional Lewis acid such as boron trifluoride, and p-toluene sulfonic acid. When a Lewis acid is employed as the catalyst, a halogen substituted solvent such as dichloromethane and chloroform may be used; and when p-toluene sulfonic acid is employed as the catalyst, a solvent such as benzene and toluene may be used. The reaction temperature may range from a room temperature to the boiling point of the solvent employed.

On the other hand, each of the optically active compounds of formulae(I') and (I'') of the present invention may be separately obtained, for example, by a process shown in the following Reaction Scheme(3):

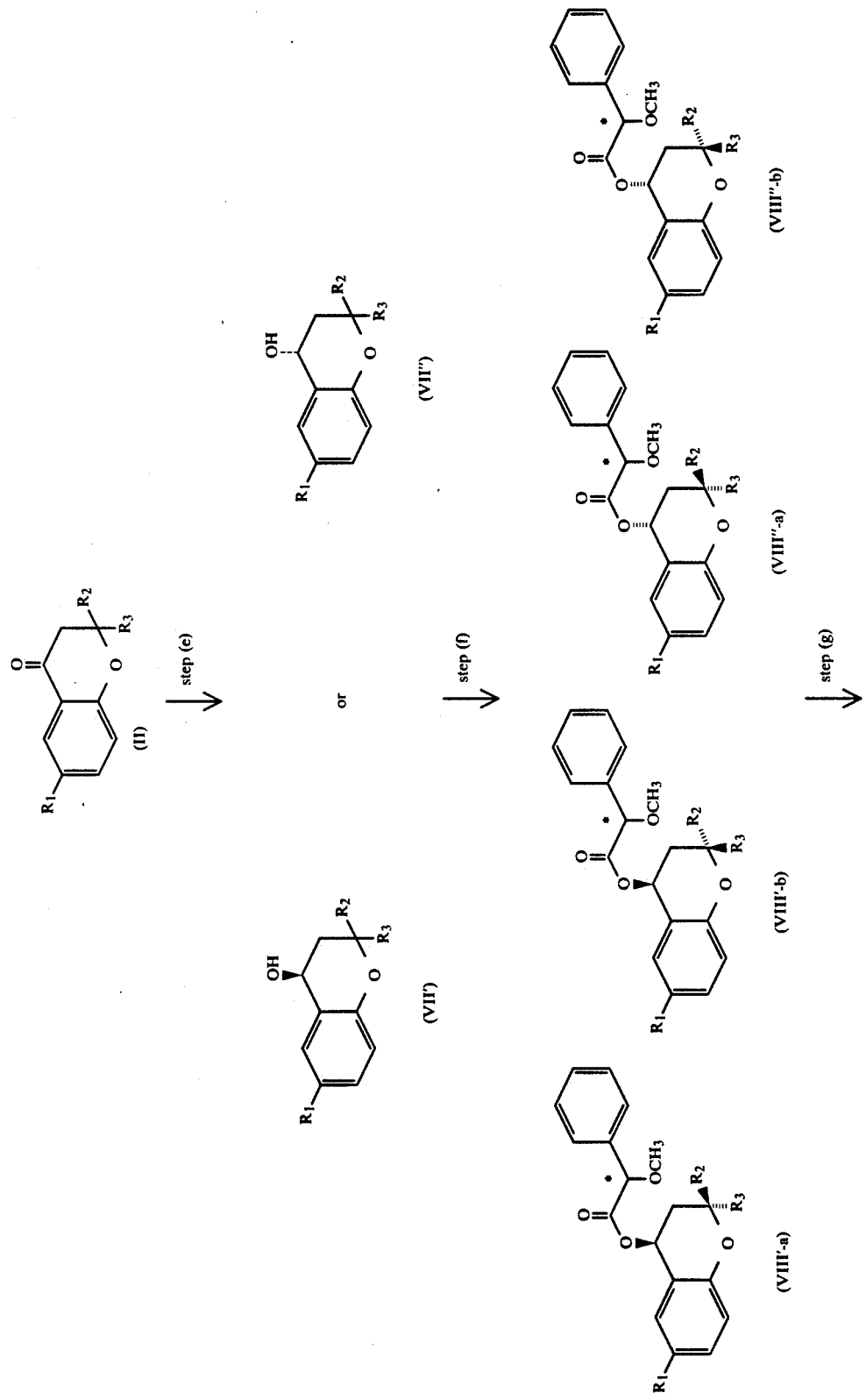

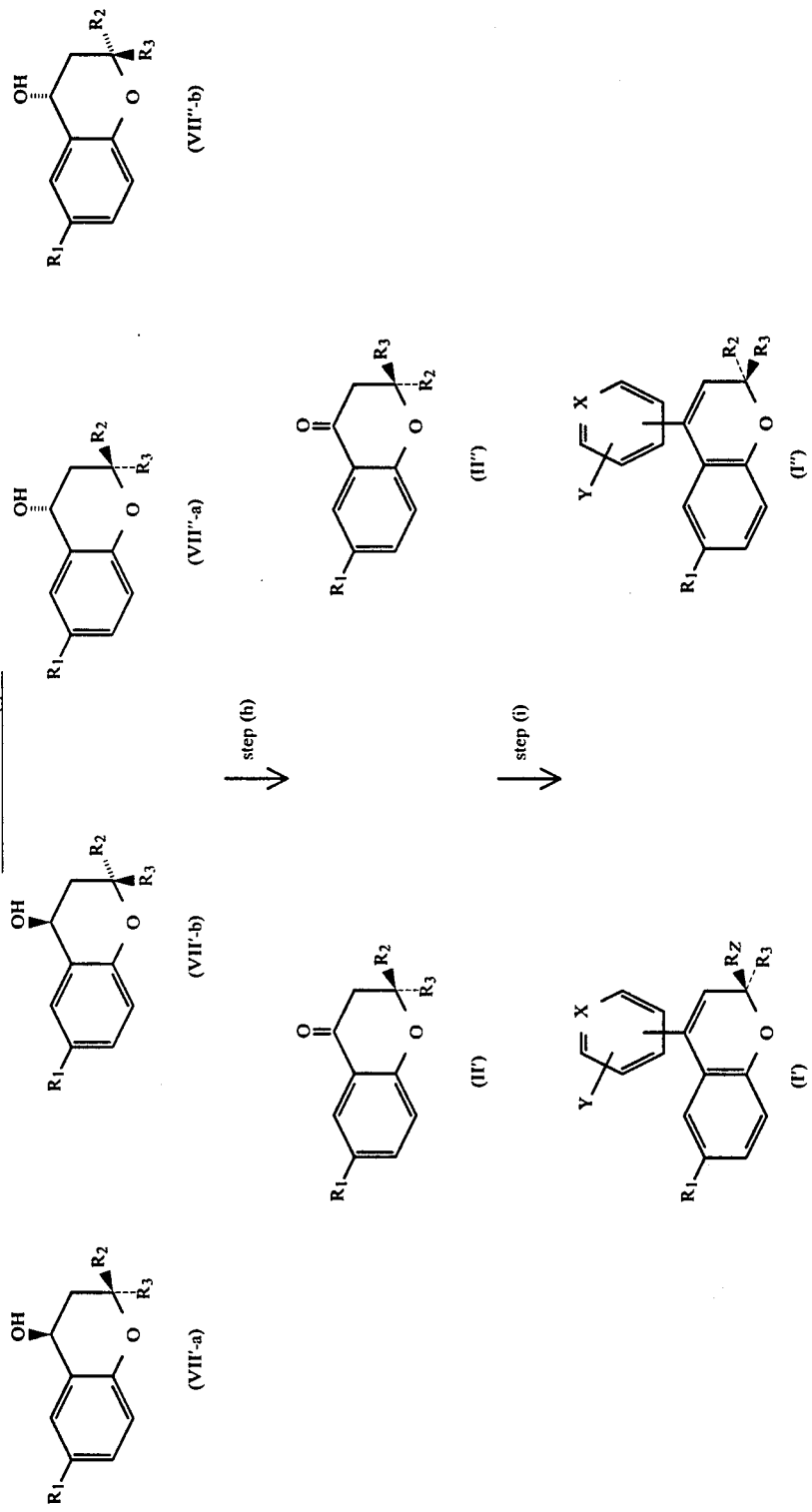

wherein $R_1$, $R_2$, $R_3$, X and Y have the same meanings as defined above.

In the above process, Step(e) may be conducted by reducing a ketone derivative of formula(II) by using a reducing agent to provide an alcoholic derivative of formula(VII); the alcoholic derivative is split into two diastereomeric alcohol mixtures of formulae(VII') and (VII") by employing chromatography. Examples of the reducing agent are sodium borohydride, zinc borohydride, diisobutyl aluminum hydride(DIBAL), L-selectride, borane, etc; and, as a solvent, ethers, tetrahydrofuran, dimethoxyethane(DME), toluene, etc. may be used. The reaction temperature may range from $-78°$ C. to a room temperature.

Then, Step(f) may be conducted by reacting each of the diastereomeric alcohol mixtures of formulae(VII') and (VII") with a chiral carbon-containing organic acid such as $(-)$-α-methoxy-α-phenylacetic acid in the presence of a condensation promoting agent and a catalyst so as to produce condenstion products; and resolving said condensation products into four separate diastereomers by employing a conventional column chromatography or a recrystallization method. The condensation promoting agent may include N, N-disubstituted carbodiimides such as N,N-dicyclohexylcarboimide and imidazols such as N,N-carbonyldiimidazole. Examples of the catalyst include 4-dimethylaminopyridin; and, a solvent such as ethyl acetate and dichloromethane may be used.

Step(g) may be conducted by hydrolyzing each of the four diastereomers to obtain the compounds of formulae(VII'-a), (VII'-b), (VII"-a) and (VII"-b), which are optically active, respectively. A base such as sodium hydroxide, potassium hydroxide, lithium hydroxide, etc.; and a solvent such as alcohols(for example, methanol), alcohol-water, THF-water, dioxane-water mixtures may be used in the hydrolysis procedure.

Step(h) may be conducted by oxidizing each of the isomers obtained in Step(g) to obtain each of the ketone derivatives of formulae(II') and (II") which are optically active. In the oxidization reaction, an oxidizing agent such as chromic trioxidepyridine, pyridinium chlorochromate(PCC), pyridinium dichromate(PDC) may be employed; and a solvent such as dichloromethane may be used. Alternatively, the oxidization may be conducted by employing a conventional method, for example, using acyl chloride, dimethylsulfoxide(DMSO) and a base.

Subsequently, Step(i) may be conducted by the same procedure as shown in the above Reaction Schemed); and the reaction conditions in this step are the same as defined in Steps(a), (b) and (c) of Reaction Schemed).

Representative examples of formula(I) of the present invention prepared by the above-mentioned processes are as follows:

2-(2"-(1"-3"-dioxolane))-2-methyl-4-(2'-pyridyl)-6-nitro-2H-1-benzopyran;
2-(2"-(1"- 3"-dioxolane))-2-methyl-4-(2'-pyridyl)-6-cyano-2H-1-benzopyran;
2-(2"-(1",3"-dioxolane))-2-methyl-4-(2'-pyridyl)-6-trifluoromethoxy-2H-1-benzopyran;
2-(2"-(1",3"-dioxolane))-2-methyl-4-(2'-pyridyl)-6-phenylsulfonylamido-2H-1-benzopyran; 2-(2"-(1"-3"-dioxolane))-2-methyl-4-(2'-pyridyl)-6-phenylsulfonyl-2H-1-benzopyran;
2-(2"-(1",3"-dioxane))-2-methyl-4-(2'-pyridyl)-6-nitro-2H-1-benzopyran;
2-(2"-(1",3"-dioxane))-2-methyl-4-(2'-pyridyl)-6-cyano-2H-1-benzopyran;
2-(2"-(1",3"-dioxane))-2-methyl-4-(2'-pyridyl)-6-trifluoromethoxy-2H-1-benzopyran;
2-(2"-(1",3"-dioxane))-2-methyl-4-(2'-pyridyl)-6-phenylsulfonylamido-2H-1-benzopyran;
2-(2"-(1",3"-dioxane))-2-methyl-4-(2'-pyridyl)-6-phenylsulfonyl-2H-1-benzopyran;
2-dimethoxymethyl-2-methyl-4-(2'-pyridyl)-6-nitro-2H-1-benzopyran;
2-dimethoxymethyl-2-methyl-4-(2'-pyridyl)-6-cyano-2H-1-benzopyran;
2-dimethoxymethyl-2-methyl-4-(2'-pyridyl)-6-trifluoromethoxy-2H-1-benzopyran;
2-dimethoxymethyl-2-methyl-4-(2'-pyridyl)-6-phenylsulfonylamido-2H-1-benzopyran;
2-dimethoxymethyl-2-methyl-4-(2'-pyridyl)-6-phenylsulfonyl-2H-1-benzopyran;
2-diethoxymethyl-2-methyl-4-(2'-pyridyl)-6-nitro-2H-1-benzopyran;
2-diethoxymethyl-2-methyl-4-(2'-pyridyl)-6-cyano-2H-1-benzopyran;
2-diethoxymethyl-2-methyl-4-(2'-pyridyl)-6-trifluoromethoxy-2H-1-benzopyran;
2-diethoxymethyl-2-methyl-4-(2'-pyridyl)-6-phenylsulfonylamido-2H-1-benzopyran;
2-diethoxymethyl-2-methyl-4-(2'-pyridyl)-6-phenylsulfonyl-2H-1-benzopyran;
2-(2"-(1",3"-dioxolane))-2-methyl-4-(2'-N-oxopyridyl)-6-nitro-2H-1-benzopyran;
2-(2"-(1",3"-dioxolane))-2-methyl-4-(2'-N-oxopyridyl)-6-cyano-2H-1-benzopyran;
2-(2"-(1",3"-dioxolane))-2-methyl-4-(2'-N-oxopyridyl)-6-trifluoromethoxy-2H-1-benzopyran;
2-(2"-(1",3"-dioxolane))-2-methyl-4-(2'-N-oxopyridyl)-6-phenylsulfonylamido-2H-1-benzopyran;
2-(2"-(1",3"-dioxolane))-2-methyl-4-(2'-N-oxopyridyl)-6-phenylsulfonyl-2H-1-benzopyran;
2-(2"-(1",3"-dioxane))-2-methyl-4-(2'-N-oxopyridyl)-6-nitro-2H-1-benzopyran;
2-(2"-(1",3"-dioxane))-2-methyl-4-(2'-N-oxopyridyl)-6-cyano-2H-1-benzopyran;
2-(2"-(1",3"-dioxane))-2-methyl-4-(2'-N-oxopyridyl)-6-trifluoromethoxy-2H-1-benzopyran;
2-(2"-(1",3"-dioxane))-2-methyl-4-(2'-N-oxopyridyl)-6-phenylsulfonylamido-2H-1-benzopyran;
2-(2 -(1",3"-dioxane))-2-methyl-4-(2'-N-oxopyridyl)-6-phenylsulfonyl-2H-1-benzopyran;
2-dimethoxymethyl-2-methyl-4-(2'-N-oxopyridyl)-6-nitro-2H-1-benzopyran;
2-dimethoxymethyl-2-methyl-4-(2'-N-oxopyridyl)-6-cyano-2H-1-benzopyran;
2-dimethoxymethyl-2-methyl-4-(2'-N-oxopyridyl)-6-trifluoromethoxy-2H-1-benzopyran;
2-dimethoxymethyl-2-methyl-4-(2'-N-oxopyridyl)-6-phenylsulfonylamido-2H-1-benzopyran;
2-dimethoxymethyl-2-methyl-4-(2'-N-oxopyridyl)-6-phenylsulfonyl-2H-1-benzopyran;
2-(2"-(1",3"-dioxolane))-2-methyl-4-(3'-pyridyl)-6-nitro-2H-1-benzopyran;
2-(2'-(1",3"-dioxolane))-2-methyl-4-(3'-pyridyl)-6-cyano-2H-1-benzopyran;
2-(2'-(1",3"-dioxolane))-2-methyl-4-(3'-pyridyl)-6-trifluoromethoxy-2H-1-benzopyran;
2-(2"-(1",3"-dioxolane))-2-methyl-4-(3'-pyridyl)-6-phenylsulfonylamido-2H-1-benzopyran;
2-(2"-(1",3"-dioxolane))-2-methyl-4-(3'-pyridyl)-6-phenylsulfonyl-2H-1-benzopyran;

2-(2''-(1'',3''-dioxane))-2-methyl-4-(3'-pyridyl)-6-nitro-2H-1-benzopyran;
2-(2''-(1'',3''-dioxane))-2-methyl-4-(3'-pyridyl)-6-cyano-2H-1-benzopyran;
2-(2''-(1'',3''-dioxane))-2-methyl-4-(3'-pyridyl)-6-trifluoromethoxy-2H-1-benzopyran;
2-(2''-(1'',3''-dioxane))-2-methyl-4-(3'-pyridyl)-6-phenylsulfonylamido-2H-1-benzopyran;
2-(2 -(1'',3''-dioxane))-2-methyl-4-(3'-pyridyl)-6-phenylsulfonyl-2H-1-benzopyran;
2-dimethoxymethyl-2-methyl-4-(3'-pyridyl)-6-nitro-2H-1-benzopyran;
2-dimethoxymethyl-2-methyl-4-(3'-pyridyl)-6-cyano-2H-1-benzopyran;
2-dimethoxymethyl-2-methyl-4-(3'-pyridyl)-6-trifluoromethoxy-2H-1-benzopyran;
2-dimethoxymethyl-2-methyl-4-(3'-pyridyl)-6-phenylsulfonylamido-2H-1-benzopyran;
2-dimethoxymethyl-2-methyl-4-(3'-pyridyl)-6-phenylsulfonyl-2H-1-benzopyran;
2,2-dimethyl-4-(3'-pyridyl)-6-nitro-2H-1-benzopyran;
2,2-dimethyl-4-(3'-pyridyl)-6-cyano-2H-1-benzopyran;
2,2-dimethyl-4-(3'-pyridyl)-6-trifluoromethoxy-2H-1-benzopyran;
2,2-dimethyl-4-(3'-pyridyl)-6-phenylsulfonylamido-2H-1-benzopyran;
2,2-dimethyl-4-(3'-pyridyl)-6-phenylsulfonyl-2H-1-benzopyran;
2-(2''-(1'',3''-dioxolane))-2-methyl-4-(3'-N-oxopyridyl)-6-nitro-2H-1-benzopyran;
2-(2''-(1'',3''-dioxolane))-2-methyl-4-(3'-N-oxopyridyl)-6-cyano-2H-1-benzopyran;
2-(2''-(1'',3''-dioxolane))-2-methyl-4-(3'-N-oxopyridyl)-6-trifluoromethoxy-2H-1-benzopyran;
2-(2''-(1'',3''-dioxolane))-2-methyl-4-(3'-N-oxopyridyl)-6-phenylsulfonylamido-2H-1-benzopyran;
2-(2''-(1'',3''-dioxolane))-2-methyl-4-(3'-N-oxopyridyl)-6-phenylsulfonyl-2H-1-benzopyran;
2-(2''-(1'',3''-dioxane))-2-methyl-4-(3'-N-oxopyridyl)-6-nitro-2H-1-benzopyran;
2-(2''-(1'',3''-dioxane))-2-methyl-4-(3'-N-oxopyridyl)-6-cyano-2H-1-benzopyran;
2-(2''-(1'',3''-dioxane))-2-methyl-4-(3'-N-oxopyridyl)-6-trifluoromethoxy-2H-1-benzopyran;
2-(2''-(1'',3''-dioxane))-2-methyl-4-(3'-N-oxopyridyl)-6-pbenylsulfonylamido-2H-1-benzopyran;
2-(2'-(1'',3''-dioxane))-2-methyl-4-(3'-N-oxopyridyl)-6-phenylsulfonyl-2H-1-benzopyran;
2-dimethoxymethyl-2-methyl-4-(3'-N-oxopyridyl)-6-nitro-2H-1-benzopyran;
2-dimethoxymethyl-2-methyl-4-(3'-N-oxopyridyl)-6-cyano-2H-1-benzopyran;
2-dimethoxymethyl-2-methyl-4-(3'-N-oxopyridyl)-6-trifluoromethoxy-2H-1-benzopyran;
2-dimethoxymethyl-2-methyl-4-(3'-N-oxopyridyl)-6-phenylsulfonyl amido-2H-1-benzopyran;
2-dimethoxymethyl-2-methyl-4-(3'-N-oxopyridyl)-6-phenylsulfonyl-2H-1-benzopyran;
2,2-dimethyl-4-(3'-N-oxopyridyl)-6-nitro-2H-1-benzopyran;
2,2-dimethyl-4-(3'-N-oxopyridyl)-6-cyano-2H-1-benzopyran;
2,2-dimethyl-4-(3'-N-oxopyridyl)-6-trifluoromethoxy-2H-1-benzopyran;
2,2-dimethyl-4-(3'-N-oxopyridyl)-6-phenylsulfonylamido-2H-1-benzopyran;
2,2-dimethyl-4-(3'-N-oxopyridyl)-6-pbenylsulfonyl-2H-1-benzopyran;
2-(2''-(1'',3''-dioxolane))-2-methyl-4-(4'-pyridyl)-6-nitro-2H-1-benzopyran;
2-(2''-(1'',3''-dioxolane))-2-methyl-4-(4'-pyridyl)-6-cyano-2H-1-benzopyran;
2-(2''-(1'',3''-dioxolane))-2-methyl-4-(4'-pyridyl)-6-trifluoromethoxy-2H-1-benzopyran;
2-(2''-(1'',3''-dioxolane))-2-methyl-4-(4'-pyridyl)-6-phenylsulfonylamido-2H-1-benzopyran;
2-(2''-(1'',3''-dioxolane))-2-methyl-4-(4'-pyridyl)-6-phenylsulfonyl-2H-1-benzopyran;
2-(2''-(1'',3''-dioxane))-2-methyl-4-(4'-pyridyl)-6-nitro-2H-1-benzopyran;
2-(2''-(1'',3''-dioxane))-2-methyl-4-(4'-pyridyl)-6-cyano-2H-1-benzopyran;
2-(2''-(1'',3''-dioxane))-2-methyl-4-(4'-pyridyl)-6-trifluoromethoxy-2H-1-benzopyran;
2-(2''-(1'',3''-dioxane))-2-methyl-4-(4'-pyridyl)-6-phenylsulfonylamido-2H-1-benzopyran;
2-(2''-(1'',3''-dioxane))-2-methyl-4-(4'-pyridyl)-6-phenylsulfonyl-2H-1-benzopyran;
2-dimethoxymethyl-2-methyl-4-(4'-pyridyl)-6-nitro-2H-1-benzopyran;
2-dimethoxymethyl-2-methyl-4-(4'-pyridyl)-6-cyano-2H-1-benzopyran;
2-dimethoxymethyl-2-methyl-4-(4'-pyridyl)-6-trifluoromethoxy-2H-1-benzopyran;
2-dimethoxymethyl-2-methyl-4-(4'-pyridyl)-6-phenylsulfonylamido-2H-1-benzopyran;
2-dimethoxymethyl-2-methyl-4-(4'-pyridyl)-6-phenylsulfonyl-2H-1-benzopyran;
2,2-dimethyl-4-(4'-pyridyl)-6-nitro-2H-1-benzopyran;
2,2-dimethyl-4-(4'-pyridyl)-6-cyano-2H-1-benzopyran;
2,2-dimethyl-4-(4'-pyridyl)-6-trifluoromethoxy-2H-1-benzopyran;
2,2-dimethyl-4-(4'-pyridyl)-6-phenylsulfonylamido-2H-1-benzopyran;
2,2-dimethyl-4-(4'-pyridyl)-6-phenylsulfonyl-2H-1-benzopyran;
2-(2''-(1'',3''-dioxolane))-2-methyl-4-(4'-N-oxopyridyl)-6-nitro-2H-1-benzopyran;
2-(2''-(1'',3''-dioxolane))-2-methyl-4-(4'-N-oxopyridyl)-6-cyano-2H-1-benzopyran;
2-(2''-(1'',3''-dioxolane))-2-methyl-4-(4'-N-oxopyridyl)-6-trifluoromethoxy-2H-1-benzopyran;
2-(2''-(1'',3''-dioxolane))-2-methyl-4-(4'-N-oxopyridyl)-6-phenylsulfonylamido-2H-1-benzopyran;
2-(2'-(1'',3''-dioxolane))-2-methyl-4-(4'-N-oxopyridyl)-6-phenylsulfonyl-2H-1-benzopyran;
2-(2 -(1 3 -dioxane))-2-methyl-4-(4'-N-oxopyridyl)-6-nitro-2H-1-benzopyran;
2-(2''-(1'',3''-dioxane))-2-methyl-4-(4'-N-oxopyridyl)-6-cyano-2H-1-benzopyran;
2-(2''-(1'',3''-dioxane))-2-methyl-4-(4'-N-oxopyridyl)-6-trifluoromethoxy-2H-1-benzopyran;
2-(2'-(1'',3''-dioxane))-2-methyl-4-(4'-N-oxopyridyl)-6-phenylsulfonylamido-2H-1-benzopyran;
2-(2''-(1',3'-dioxane))-2-methyl-4-(4'-N-oxopyridyl)-6-phenylsulfonyl-2H-1-benzopyran;
2-dimethoxymethyl-2-methyl-4-(4'-N-oxopyridyl)-6-nitro-2H-1-benzopyran;
2-dimethoxymethyl-2-methyl-4-(4'-N-oxopyridyl)-6-cyano-2H-1-benzopyran;
2-dimethoxymethyl-2-methyl-4-(4'-N-oxopyridyl)-6-trifluoromethoxy-2H-1-benzopyran;
2-dimethoxymethyl-2-methyl-4-(4'-N-oxopyridyl)-6-phenylsulfonylamido-2H-1-benzopyran;
2-dimethoxymethyl-2-methyl-4-(4'-N-oxopyridyl)-6-phenylsulfonyl-2H-1-benzopyran;

2,2-dimethyl-4-(4'-N-oxopyridyl)-6-nitro-2H-1-benzopyran;

2,2-dimethyl-4-(4'-N-oxopyridyl)-6-cyano-2H-1-benzopyran;

2,2-dimethyl-4-(4'-N-oxopyridyl)-6-trifluoromethoxy-2H-1-benzopyran;

2,2-dimethyl-4-(4'-N-oxopyridyl)-6-phenylsulfonylamido-2H-1-benzopyran;

2,2-dimethyl-4-(4'-N-oxopyridyl)-6-phenylsulfonyl-2H-1-benzopyran;

As mentioned above, the compounds of formula(I) of the present invention have excellent effectiveness in the treatment of hypertension by lowering blood pressure with a relaxation activity on vascular smooth muscle; and, further, in the treatment of asthma by relaxing respiratory smooth muscle.

The present invention also provides pharmaceutical compositions containing the compounds of formula(I) of the present invention as an active ingredient. Particularly, the present invention provides pharmaceutical compositions containing an effective amount of the compounds of formula(I) and conventional and pharmaceutically acceptable carriers.

The composition of the present invention can be formulated for oral or other foms of administration, preferably oral administration. The formulated composition are preferably in the form of a unit dose. Examples of suitable unit dose forms may tablet, capsule and powder. The effective unit-dose may comprise 0.1 to 10 mg, preferably 1 to 5 mg of the compound of the present invention.

The composition of the present invention may be formulated with conventional additives, for example a filler, dispersant, binder, lubricant, favoring agent, etc. The formulation of the composition can be conducted by using a known method in the art.

The following Preparation Examples and Examples are intended to illustrate how some of the compounds of the present invention can be prepared, without limiting its scope of the invention.

EXAMPLE 1

Synthesis of
2,2-dimethyl-4-(3'-pyridyl)-6-nitro-2H-1-benzopyran

Step 1) Synthesis of
2,2-dimethyl-4-(O-triflate)-6-nitro-2H-1-benzopyran

To a solution of 1.09 (4.52 mmole) of 2,2-dimethyl-6-nitropropanone dissolved in 50 ml of dichloromethane was added 1.1 ml (6.78 mmole) of anhydrous trifluorosulfonic acid under argon atmospheric environment. To the resultant mixture was slowly added a solution of 1.39 g (6.78 mmole) of 2,6-di-t-butyl-4-methylpyridine dissolved in 3 ml of distilled dichloromethane, which was stirred for 20 hours at room temperature. After completion of the reaction, the reaction mixture was diluted with 50 ml of dichloromethane and washed with a saturated sodium chloride solution (20 ml×2). The organic layer was dried over anhydrous MgSO$_4$, concentrated and purified by silica gel column chromatography using a mixture of hexane and ethyl acetate (8:1) as an eluent to obtain 1.13 g (3.20 mmole, yield 71%) of the title compound.

$^1$H NMR (CDCl$_3$).

δ1.60 (s, 6H, C(CH$_3$)$_2$), 5.80 (s, 1H, H-3), 6.95 (d, 1H, aromatic), 7.60 (m, 2H, aromatic).

Step 2) Synthesis of
2,2-dimethyl-4-(3'-pyridyl)-6-nitro-2H-1-benzopyran

In flask 0.38 g (9.04 mmole) of anhydrous lithium chloride was dried sufficiently. Then, 46 mg (0.045 mmole) of dipalladium tridebenzylidine acetone chloroform (Pd$_2$ (dba)$_3$ (CHCl$_3$)) and 47 mg (0.18 mmole) of triphenylphosphine were added thereto. The reactants were dissolved in 15 ml of distilled tetrahydrofuran under argon atmosphere. Subsequently, a solution of 0.40 g (1.13 mmole) of the triflate compound obtained in step 1 dissolved in 3 ml of distilled tetrahydrofuran and a solution of 0.50 g (1.36 mmole) of tributyl (3-pyridyl)-tin dissolved in 2 ml of distilled tetrahydrofuran were added in succession thereto. The resultant solution was heated to reflux for 40 hours, cooled and extracted with 50 ml of ethyl acetate. The organic layer was dried over anhydrous Na$_2$SO$_4$, concentrated and purified by silica gel column chromatography using a mixture of hexane and ethyl aceate (3:1) as an eluent to obtain 0.19 g (0.67 mmole, yield 59%) of the desired compound.

$^1$H NMR (CDCl$_3$).

δ1.58 (s, 6H, CMe$_2$), 5.78 (s, 1H, H-3), 6.95 (d, 1H, aromatic), 7.39 (m, 1H,aromatic), 7.68 (m, 1H, aromatic), 7.82 (d, 1H, aromatic), 8.10 (dd, 1H,aromatic),8.61 (dd, 1H,aromatic), 8.68 (dd, 1H, aromatic).

EXAMPLE 2

Synthesis of
2,2-dimethyl-4-(3'-N-oxopyridyl)-6-nitro-2H-1-benzopyran

To a solution of 89 mg (0.32 mmole) of the compound obtained in Example 1 above dissolved in a mixture of 2 ml of acetone and 2 ml of distilled water was added 270 mg (3.20 mmole) of NaHCO$_3$. 200 mg of oxon was slowly added at room temperature thereto. The resultant reaction solution was stirred for 20 minutes and extracted with 10 ml of ethyl acetate. The organic layer was dried over anhydrous Na$_2$SO$_4$, concentrated and purified by silica gel column chromatography using a mixture of methanol and dichloromethane (9:1) as an eluent to obtain 70 mg (0.23 mmole, yield 72%) of the desired compound.

$^1$H NMR (CDCl$_3$).

δ1.53 (s, 6H, CMe$_2$), 5.81 (s, 1H, H-3), 6.96 (d, 1H,aromatic), 7.21 (m, 1,aromatic),7.38 (m, 1H,aromatic),7.80 (d, 1H,aromatic), 8.10 (dd, 1H,aromatic),8.25 (dd, 1H, aromatic).

EXAMPLE 3

Synthesis of
2,2-dimethyl-4-(4'-pyridyl)-6-nitro-2H-1-benzopyran

In 5 ml of flask 0.352 g (8.38 mmole) of anhydrous lithium chloride was dried sufficiently under reduced pressure; and, 87 mg (0.084 mmole) of Pd$_2$ (dba)$_3$ (CHCl$_3$) and 88 mg (0.335 mmole) of triphenylphosphine were added thereto. The reactants wer dissolved in 10 ml of dry tetrahydrofuran under argon atmosphere. Subsequently, a solution of 2.64 g (8.3 mmole) of the triflate obtained in step 1 of Example 1 dissolved in 6 ml of tetrahydrofuran was added. After stirring for 5 minutes, a solution of 0.303 g (1.256 mmole) of trimethyl (4-pyridyl)tin dissolved in 6 ml of distilled tetrahydrofuran was added thereto. The resultant solution was heated to reflux for 12 hours; and, the reaction was terminated. From the reaction mixture tetrahydrofuran was removed under reduced pressure. The residue so obtained was diluted with 20 mg of water and extracted with ethyl acetate (50 mg×3). The organic layer was dried over anhydrous Na₂SO₄, concentrated and purified by silica gel column chromatography using a mixture of hexane and ethyl aceate (2:1) as an eluent to obtain 0.160 g (yield 68%) of the desired compound.

EXAMPLE 4

Synthesis of 2,2-dimethyl-4-(4'-N-oxopyridyl)-6-nitro-2H-1-benzopyran

To a solution of 140 mg (0.496 mmole) of the compound obtained in Example 3 above dissolved in a mixture of 5 ml of acetone and 5 ml of distilled water was added 0.467 mg (4.96 mmole) of NaHCO₃3. 0.305 g of oxon was slowly added at room temperature thereto. The resultant solution was stirred for 30 minutes, removed acetone solvent under reduced pressure and extracted with ethyl acetate (30 ml×3). The organic layer was dried over anhydrous Na₂SO₄, concentrated and purified by silica gel column chromatography using a mixture of methanol and dichloromethane (1:9) as an eluent to obtain 0.130 g (yield 90%) of the desired compound.

¹H NMR (CDCl₃).

δ1.55 (s, 6H, (—CH₃)₂), 5.85 (s, 1H, H-3), 7.0 (d, 1H,aromatic), 7.3 (d, 2H,aromatic),7.9 (d, 1H,aromatic),8.15 (dd, 1H,aromatic), 8.3 (m, 2H, aromatic).

EXAMPLE 5

Synthesis of 2,2-dimethyl-4-(3'-pyridyl)-6-cyano-2H-1-benzopyran

Step 1) Synthesis of 2,2-dimethyl-4-(O-triflate)-6-cyano-2H-1-benzopyran

To a solution of 1.0 g (4.98 mmole) of 2,2-dimethyl-6-cyanochromanone dissolved in 6 ml of distilled dichloromethane was added 1.3 ml (7.46 mmole) of anhydrous trifluorosulfonic acid under argon atmosphere. To the resultant mixture was slowly added a solution of 1.5 g (7.46 mmole) of 2,6-di-t-butyl-4-methylpyridine dissolved in 3 ml of distilled dichloromethane, which was stirred for 24 hours at room temperature. After completion of the reaction, the reaction mixture was diluted with 5 ml of dichloromethane and washed with saturated sodium chloride solution (2 ml×2). The organic layer was dried over anhydrous MgSO₄, concentrated and purified by silica gel column chromatography using a mixture of hexane and ethyl acetate (6:1) to obtain 914 mg (3.20 mmole, yield 55%) of the title compound as an ivory solid.

¹H NMR (CDCl₃).

δ1.60 (s, 6H, C(CH₃)₂) 5.75 (s, 1H, H-3), 7.50 (m, 3H, aromatic).

Step 2) Synthesis of 2,2-dimethyl-4-(3'-pyridyl)-6-cyano-2H-1-benzopyran

In 2-neck round bottom flask 444 mg (10.6 mmole) of anhydrous lithium chloride was dried sufficiently by heating through vaccum pump; and, 68 mg (0.07 mmole) of Pd₂ (dba)₃ (CHCl₃) and 69 mg (0.26 mmole) of triphenylphosphine were added thereto. The reactants were dissolved in 10 ml of distilled tetrahydrofuran under argon atmosphere. Subsequently, a solution of 440 mg (1.32 mmole) of the triflate compound obtained in step 1 and 538 mg (1.58 mmole) of tributyl (3-pyridyl)tin dissolved in 6 ml of distilled tetrahydrofuran was added thereto. The resultant solution was heated to reflux for 24 hours, cooled and extracted with 30 ml of ethyl acetate. The organic layer was dried over anhydrous Na₂SO₄, concentrated and purified by silica gel column chromatography using a mixture of hexane and ethyl aceate (2:1) as an eluent to provide 200 mg (yield 58%) of the desired compound as a yellow oil.

EXAMPLE 6

Synthesis of 2,2-dimethyl-4-(3'-N-oxopyridyl)-6-cyano-2H-1-benzopyran

To a solution of 100 mg (0.38mmole) of the compound obtained in Example 5 above dissolved in 2 ml of acetone were added 2 ml of distilled water and 319 mg (3.8mmole) of NaHCO₃, which was stirred for about 10 minutes. 234 mg (0.38mmole) of oxon was slowly added at room temperature thereto. The resultant solution was stirred for 1 hour, extracted with 20 ml of ethyl acetate and washed with 10 ml of saturated sodium chloride solution. The organic layer was dried over anhydrous Mg₂SO₄, concentrated under reduced pressure and purified by silica gel column chromatography using a mixture of methanol and dichloromethane (3:97) as an eluent to obtain 75 mg (yield 71%) of the desired compound as a white solid.

¹H NMR (CDCl₃).

δ1.55 (s, 6H, (CH₃)2), 5.8 (s, 1H, H-3), 6.96 (d, 1H,aromatic), 7.25 (m, 2H,aromatic),7.4 (m, 1H,aromatic),7.7 (dd, 1H, aromatic), 8.25 (m, 2H,aromatic).

EXAMPLE 7

Synthesis of 2,2-dimethyl-4-(4'-pyridyl)-6-cyano-2H-1-benzopyran

In 50 ml of flask 0.672 g (16mmole) of anhydrous lithium chloride was dried sufficiently under reduced pressure; and, 60 mg (0.06 mmole) of Pd₂ (dba)₃ (CHCl₃) and 106 mg (0.4 mmole) of triphenylphosphine were added thereto. The reactants were dissolved in 10 ml of dry tetrahydrofuran under argon atmosphere. Subsequently, a solution of 430 mg (1.6 mmole) of the triphlate obtained in step 1 of Example 5 above dissolved in 6 ml of tetrahydrofuran was added. After stirring for 5 minutes, a solution of 0.6 g (2.48 mmole) of trimethyl (4-pyridyl) tin dissolved in 6 ml of distilled tetrahydrofuran was added thereto. The resultant solution was heated to reflux for 12 hours and the reaction was terminated. The reaction mixture was evaporated under reduced pressure to remove tetrahydrofuran and extracted with ethyl acetate (50 ml×3). The organic layer was dried over anhydrous Na₂SO₄, concentrated and purified by silica gel column chromatography using a mixture of hexane and ethyl aceate (3:1) as an eluent to obtain 0.26 g (yield 50%) of the desired compound.

EXAMPLE 8

Synthesis of 2,2-dimethyl-4-(4'-N-oxopyridyl)-6-cyano-2H-1-benzopyran

To a solution of 100 mg (0.383 mmole) of the compound obtained in Example 7 above dissolved in a mixture of 10 ml of acetone and 10 ml of distilled water was added 0.32(3.825 mmole) of NaHCO₃ thereto. 0.235(0.383 mmole) of oxon was slowly added at room temperature thereto. The resultant solution was stirred for 30 minutes, evaporated under reduced pressure to remove acetone solvent and extracted with ethyl acetate (30 ml×3). The organic layer was dried over anhydrous Na$_2$SO$_4$, concentrated and purified by silica gel column chromatography using a mixture of methanol and dichloromethane (5:95) as an eluent to obtain 95 mg (yield 90%) of the desired compound.

$^1$H NMR (CDCl$_3$).

δ1.55 (s, 6H, (—CH$_3$)$_2$), 5.8 (s, 1H, H-3), 6.96 (d, 1H, aromatic), 7.25 (m, 2H,aromatic),7.4 (m, 1H,aromatic)3 7.7 (dd, 1H, aromatic), 8.25 (m, 2H, aromatic).

EXAMPLE 9

Synthesis of 2-dimethoxymethyl-2-methyl-(2'-pyridyl) 6-nitro-2H-1-benzopyran

Step 1) Synthesis of 2-dimethoxymethyl-2-methyl-4-oxo-3,4-dihydro-2H-1-benzopyran In 250 ml of toluene were dissolved 30 g (0.22 mmole) of 2-hydroxy acetophenone and 33.8(0.29 mmole) of pyruvic aldehyde dimethyl acetal; and, 6.3 ml (0.09 mmole) of pyridine was added thereto. After stirring at room temperature 30 minutes, the reactants were heated to reflux for 5 hours using Dean-Stark apparatus. The solvent was removed under reduced pressure and 100 ml of 2N HCl aqueous solution was added. The resultant solution was stirred for 1 hour at room temperature, extracted with ethyl acetate (20 ml×2), washed with 100 ml of water and then with 50 ml of saturated sodium chloride aqueous solution and purified by silica gel column chromatography using a mixture of hexane and ethyl acetate (4:1) to obtain 39 g (0.16 mmole, yield 75%) of the title compound as a white solid.

Step 2) Synthesis of 2-dimethoxymethyl-2-methyl-4-oxo-6-nitro-3,4-dihydro-2H-1-benzopyran In 15 ml of chloroform were dissolved 1.99 (8.1 mmole) of the compound obtained in step 1 and 0.64(8.1 mmole) of ammonium nitrate; and, 4.5 ml (32 mmole) of anhydrous trifluoroacetic acid was added thereto at room temperature. The resultant mixture was stirred at room temperature for 3 hours; and, the reaction was terminated with a saturated NaHCO$_3$ aqueous solution. The resultant solution was extracted with dichloromethane (50 ml×2), washed with 50 ml of water and with 20 ml of saturated sodium chloride solution, dried over anhydrous magnesium sulfate, filtered and concentrated to obtain residue, which was purified by silica gel column chromatography using a mixture of hexane and ethyl acetate (4:1) as an eluent to obtain 1.24 g (yield 55%) of the title compound.

Step 3) Synthesis of 2-dimethoxymethyl-2-methyl-4-(O-triflate)-6-nitro-2H-1-benzopyran In a dried flask, 2.8 ml of (19.5 mmole) of diisopropylamine was dissolved in 20 ml of distilled THF and 6 ml of dimethoxyethane. To the resultant solution was slowly added 7.8 ml (19.5 mmole) of 2.5M solution of n-butyl lithium dissolved in hexane at −78° C. The resultant mixture was stirred for 10 minutes. A solution of 4.02 g (13.0 mmole) obtained in step 2 dissolved in 20 ml of dimethoxyethane was slowly added thereto. The resultant mixture was slowly warmed up to 0° C. and stirred for 1 hour. A solution of 5.57 g (15.6 mmole) of N-phenyl trifluoromethane sulfonimide dissolved in 2 ml of dimethoxyethane was slowly added to the above mixture, which was stirred for 6 hours at 0° C. The resultant mixture was diluted with 100 ml of ethyl acetate and washed with 30 ml of saturated sodium chloride solution. The organic layer was dried over anhydrous magnesium sulfate, evaporated to remove the solvent and purified by silica gel column chromatography using a mixture of hexane and ethyl acetate (4:1) as an eluent to obtain 4.29 g9.73 mmole, yield 75%) of the title compound.

Step 4) Synthesis of 2-dimethoxymethyl-2-methyl-4-(2'-pyridyl)-6-nitro-2H-1-benzopyran In dried flask 1.62 g38.8 mmole) of anhydrous lithium chloride was dried sufficiently by vacuum pump for 30 minutes; and, 83 mg (0.073 mmole) of tetrakis triphenylphosphine palladium (Pd (PPh$_3$)$_4$) was added under argon atmosphere. The reactants were dissolved in 20 ml of distilled tetrahydrofuran. The reaction solution was stirred for 10 minutes at room temperature. Subsequently, a solution of 2.14 g4.85 mmole) of the triflate obtained in step 1 dissolved in 15 ml of distilled tetrahydroufuran and a solution of 2.68 g (7.28 mmole) of tributyl (2-pyridyl)tin dissolved in 10 ml of distilled tetrahydrofuran were added in turn thereto. The resultant solution was heated to reflux for 15 hours, cooled by standing out at room temperature and extracted with 50 ml of ethyl acetate. The organic layer was dried over anhydrous MgSO$_4$, concentrated and purified by silica gel column chromatography using a mixture of hexane and ethyl aceate (2:1) as an eluent to obtain 1.44 g (3.89 mmole, yield 80%) of the desired compound.

$^1$H NMR (CDCl$_3$, 300 MHz)δ 1.53 (s, 3H, C(CH$_3$)$_2$), 3.50 (s, 3H, CH (OCH$_3$)2), 3.58 (s, 3H, CH(OCH$_3$)$_2$), 4.33 (s, 1H, CH(OCH$_3$)2), 6.05 (s, 1H, H-3), 6.95 (d, 1H,aromatic),7.33 (m, 1H,aromatic),7.48 (dd, 1H,aromatic), 7.80 (t, 1H,aromatic),8.07 (dd, 1H,aromatic),8.29 (dd, 1H,aromatic), 8.72 (dd, 1H,aromatic).

EXAMPLE 10

Synthesis of 2-dimethoxymethyl-2-dimethyl-4-(2'-N-oxopyridyl)-6-nitro-2H-1-benzopyran To a solution of 0.50 g (1.35 mmole) of the compound obtained in Example 9 above dissolved in 7 ml of dichloromethane was added 0.239 g (2.70 mmole) of NaHCO$_3$. At 0° C., 0.43(2.03 mmole) of 85% m-chloroperbenzoic acid was slowly added thereto. The resultant mixture was stirred for 2 hours, diluted with 20 ml of dichloromethane,15 washed with 10 ml of saturated Na$_2$SO$_3$.5H$_2$O solution, 10 ml of 1.0N NaOH and then 10 ml of saturated sodium chloride solution. The organic layer was dried over anhydrous Na$_2$SO$_4$, concentrated and purified by silica gel column chromatography using a mixture of methanol and dichloromethane (1:19) as an eluent to obtain 0.31 g (0.80 mmole, yield 59%) of the desired compound.

$^1$H NMR (CDCl$_3$, 300 MHz)δ 1.57 (s, 3H, C(CH$_3$)$_2$), 3.50 (s, 3H, CH(OCH$_3$)$_2$), 3.59 (s, 3H, CH(OCH$_3$)$_2$), 4.39 (s, 1H, CH(OCH$_3$)2), 5.99 (s,1H, H-3), 6.93 (m, 2H, aromatic),7.40 (m, 4H, aromatic), 8.28 (dd, 1H, aromatic).

EXAMPLE 11

Synthesis of 2-dimethoxymethyl-2-methyl-4-(2'-pyridyl) 6-cyano-2H-1-benzopyran

Step 1) Synthesis of 2-dimethoxymethyl-2-methyl-4-oxo-6-cyano-3,4-dihydro-2H-1-benzopyran In 100 ml of toluene were dissolved 8.06 g (50 mmole) of 3-acetyl-4-hydroxybenzonitrile and 7.68 g (65 mmole) of pyruvic aldehyde dimethyl acetal; and, 1.67 ml (20 mmole) of pyrrolidine was added at room temperature thereto. 30 Minutes thereafter, the reactants were heated to reflux for 8 hours using Dean-Stark apparatus. The solvent was removed under reduced pressure; and, 50 ml of 2N HCl solution was added to the residue so obtained. The resultant solution was stirred for 30 minutes at room temperature, extracted with ethyl acetate (100 ml×2), washed with 50 ml of water and then with 50 ml of saturated sodium chloride aqueous solution and purified by silica gel column chromatography using as an eluent a mixture of hexane and ethyl acetate (4:1) to obtain 11.19 g (yield 86%) of the title compound as a white solid.

Step 2) Synthesis of 2-dimethoxymethyl-2-methyl-4-(O-triflate)-6-cyano-2H-1-benzopyran Similarly to the procedures described in step 3 of Example 9 above, the title compound was prepared.

Step 3) Synthesis of 2-dimethoxymethyl-2-methyl-4-(2'-pyridyl)-6-cyano-2H-1-benzopyran Similarly to the procedures described in step 4 of Example 9 above, the desired compound was prepared.

$^1$H NMR (CDCl$_3$, 300 MHz)δ 1.50 (s, 3H, H-2), 3.50 (s, 3H, CH(OCH$_3$)$_2$), 3.53 (s, 3H, CH(OCH$_3$)$_2$), 4.33 (s, 1H, CH(OCH$_3$)$_2$), 6.02 (s, 1H, H-3), 6.92 (d, 1H, aromatic), 7.24 (m, 3H, aromatic), 7.82 (m, 2H, aromatic), 8.70 (dd, 1H, aromatic).

EXAMPLE 12

Synthesis of 2-dimethoxymethyl-2-methyl-4-(2'-N-oxopyridyl)-6-cyano-2H-1-benzopyran Similarly to the procedures described in Example 10 above, the desired compound was prepared using the end product of Example 11.

$^1$H NMR (CDCl$_3$, 300 MHz)δ 1.54 (s, 3H, H-2), 3.50 (s, 3H, CH(OCH$_3$)$_2$), 3.57 (s, 3H, CH(OCH$_3$)$_2$), 4.39 (s, 1H, CH(OCH$_3$)$_2$), 5.96 (s, 1H, H-3), 6.93 (m, 2H, aromatic), 7.40 (m, 4H, aromatic), 8.35 (dd, 1H, aromatic).

EXAMPLE 13

Synthesis of 2-dimethoxymethyl-2-methyl-4-(2'-pyridyl)-phenylsulfonyl-2H-1-benzopyran

Step 1) Synthesis of 4-phenylsulfonyl-1-methoxybenzene

To a solution of 16 g of AlCl$_3$ dissolved in 21.6 g of anisol was added dropwise 17.6 g of benzenesulfonyl chloride. The reaction mixture was heated to reflux for 8 hours and poured into 1N HCl solution containing ice. The resultant solution was extracted with ethyl acetate (100 ml×3), washed with 100 ml of saturated NaHCO$_3$ aqueous solution, dried over Na$_2$SO$_4$ and concentrated to obtain residue, which was recrystallized from hexane-ethyl acetate to obtain 25 g of the title compound.

Step 2) Synthesis of 4-phenylsulfonyl-1-hydroxybenzene

To a solution of 24.8 g (100 mmole) of the compound obtained in step 1 dissolved in 50 ml of acetic acid was added 40% HBr, which was heated to reflux for 8 hours. The reaction solution was poured into ice-water. The resultant solution was extracted with ethyl acetate (100 ml×3), dried over Na$_2$SO$_4$ and concentrated to obtain residue, which was purified by silica gel column chromatography using a mixture of hexane and ethyl acetate (1:1) to obtain 23.0 g (yield 100%) of the title compound containing a portion of orthoisomer (approximately one-eighth).

Step 3) Synthesis of 4-phenylsulfonyl-1-acetoxybenzene

In 150 ml of CH$_2$Cl$_2$ were dissolved 23 g of the compound obtained in step 2; and, 12.9 ml of pyridine and 7.8 ml of acetyl chloride was slowly added at room temperature thereto. The reaction solution was washed with 0.2N HCl and with saturated NaHCO$_3$ aqueous solution, dried over Na$_2$SO$_4$ and concentrated under reduced pressure to obtain residue, which was used for subsequent reaction without further purification.

Step 4) Synthesis of 4-phenylsulfonyl-2-acetylphenol

To a solution of 0.67 g of the compound obtained in step 3 dissolved in 5 ml of CS$_2$ was added 0.97 g of AlCl$_3$. The reaction mixture was heated to the temperature of 190° C. (at this temperature, CS$_2$ would be distilled) and maintained at that temperature for 30 minutes. The reaction mixture was poured into 1N HCl solution containing ice. The resultant solution was extracted with ethyl aceate (20 ml×3), dried over Na$_2$SO$_4$ and concentrated under reduced pressure to obtain residue, which was purified by silica gel column chromatography using a mixture of hexane and ethyl acetate (2:1) as an eluent to obtain 0.35 g (yield 52%) of the title compound.

Step 5) Synthesis of 2-dimethoxymethyl-2-methyl-4-oxo-6-phenylsulfonyl-3,4-dihydro-2H-1-benzopyran In 100 ml of toluene were dissolved 10 g of the compound obtained in step 4, 6.5 ml of pyruvic aldehyde dimethyl acetal and 1.5 ml of pyrrolidine. The resultant solution was heated to reflux for 16 hours and concentrated reduced pressure to obtain residue, which was purified by silica gel column chormatography using as an eluent a mixture of hexane and ethyl acetate (2:1) to obtain 11 g of the title compound.

Step 6) Synthesis of 2-dimethoxymethyl-2-methyl-4-(O-triflate)-6-phenylsulfonyl-2H-1-benzopyran Similarly to the step 3 of Example 9 above, the title compound was prepared using the compound obtained in step 5.

Step 7) Synthesis of 2-dimethoxymethyl-2-methyl-4-(2'-pyridyl)-6-phenylsulfonyl-2H-1-benzopyran Similarly to the procedures described in step 4 of Example 9 above, the desired compound was prepared.

¹H NMR (CDCl₃)δ1.50 (s, 3H, CH₃), 3.48 (s, 3H, CH(OCH₃)₂), 3.53 (s, 3H, CH(OCH₃)₂), 4.50 (s, 1H, CH(OCH₃)₂), 5.80 (s, 1H, H-3), 6.95 (d, 1H, aromatic), 7.48 (m, 7H, aromatic), 7.66 (dd, 1H, aromatic), 7.87 (m, 2H,aromatic),8.31 (m, 1H,aromatic).

EXAMPLE 14

Synthesis of 2-dimethoxymethyl-2-methyl-4-(2'-N-oxopyridyl)-6-phenylsulfonyl-2H-1-benzopyran Similarly to the procedures described in Example 10 above, the desired compound was prepared using the end product of Example 13.

¹H NMR (CDCl₃)δ1.50 (s, 3H, CH₃), 3.48 (s, 3H, CH(OCH₃)₂), 3.55 (s, 1H, CH(OCH₃)₂), 5.98 (s, 1H, H-3), 6.93 (d, 1H,aromatic, 7.45 (m, 7H, aromatic), 7.64 (dd, 1H,aromatic),7.89 (m, 2H,aromatic), 8.33 (m, 1H, aromatic).

EXAMPLE 15

Synthesis of 2-dimethoxymethyl-2-methyl-(2'-pyridyl)-6-trifluoromethoxy-2H-1-benzopyran Step 1) Synthesis of 4-trifluoromethoxy-2-(α-hydroxyethyl)phenol To a solution of 1.0 g (4.85 mmole) of 5-(trifluoromethoxy) salicyl aldehyde dissolved in 500 ml of dry ether was slowly added 10.34 ml (14.55 mmole) of 1.4M CH₃Li at room temperature. The resultant solution was stirred for 30 minutes at room temperature and 1N HCl was added thereto to acidify the solution. The acidified solution was extracted with ethyl acetate (20 ml×3), dried and concentrated to obtain residue, which was purified by silica gel column chromatography using as an eluent a mixture of hexane and ethyl acetate of 2:1 to obtain the 0.889 g (yield 82%) of title compound.

Step 2) Synthesis of 4-trifluoromethoxy-2-acetylphenol

In 20 ml of dichloromethane was dissolved 0.85 g (3.83 mmole) of the compound obtained in step 1; and, a suitable amount of Cellite and 1.73 g (4.6 mmole) of pyridinium dichromate were added thereto. The resultant mixture was stirred for 30 minutes at room temperature and filtered by a Cellite layer to obtain precipitates, which were purified by silica gel column chromatography using as an eluent a mixture of hexane and ethyl acetate of 6:1 and then concentrated under reduced pressure at 0° C. to obtain 0.72 g (yield 85%) of the title compound.

Step 3) Synthesis of 2-dimethoxymethyl-2-methyl-4-oxo-6-trifluoromethoxy-3,4-dihydro-2H-1-benzopyran To a solution of 0.5 g (2.27 mmole) of the compound obtained in step 2 dissolved in 10 ml of toluene were added 0.55 ml (4.54 mmole) of pyruvic aldehyde dimethyl acetal and 80 mg (1.14 mmole) of pyrrolidine. The reactants were heated to reflux for about 12 hours using Dean-Stark apparatus. After completion of the reaction, toluene solvent was removed therefrom under reduced pressure. The residue so obtained was extracted with ethyl acetate and concentrated to give residue, which was purified by silica gel column chromatography using as an eluent a mixture of hexane and ethyl acetate of 10:1 to obtain 0.470 g (yield 65%) of the title compound.

¹H NMR (CDCl₃, 200 MHz)δ1.6 (d, 3H), 2.6 (d, 1H), 5.1 (m, 1H), 6.85 (m, 2H), 7.1 (m, 1H), 8.1 (s, 1H).

Step 4) Synthesis of 2-dimethoxymethyl-2-methyl-4-(O-triflate)-6-trifluoromethoxy-2H-1-benzopyran Similarly to the step 3 of Example 9 above, the title compound was prepared.

Step 5) Synthesis of 2-dimethoxymethyl-2-methyl-4-(2'-pyridyl)-6-trifluoromethoxy-2H-1-benzopyran Similarly to the procedures described in step 4 of Example 9 above, the desired compound was prepared.

¹H NMR (CDCl₃) δ1.50 (s, 3H, CH₃), 3.51 (s, 3H, CH(OCH₃)₂), 3.58 (s, 3H, CH(OCH₃)₂), 4.38 (s, 1H, CH(OCH₃)₂), 6.04 (s, 1H, H-3), 6.98 (d, 1H,aromatic),7.03 (m, 1H,aromatic),7.20 (d, 1H, aromatic), 7.31 (m, 1H,aromatic),7.45 (dd, 1H,aromatic),7.78 (m, 1H, aromatic), 8.70 (m, 1H,aromatic).

EXAMPLE 16

Synthesis of 2-dimethoxymethyl-2-methyl-4-(2'-N-oxopyridyl)-6-trifluoromethoxy-2H-1-benzopyran Similarly to the procedures described in Example 10 above, the desired compound was prepared using the end product of Example 15.

¹H NMR (CDCl₃) δ1.50 (s, 3H, CH₃), 3.51 (s, 3H, CH(OCH₃)₂), 3.54 (s, 3H, CH(OCH₃)₂), 5.30 (s, 1H, CH(OCH₃)₂), 5.97 (s, 1H, H-3), 6. 90 (d, 1H, aromatic),7.00 (m, 1H, aromatic), 7.22 (d, 1H, aromatic),7.32 (m, 1H, aromatic), 7.46 (dd, 1H, aromatic), 7.80 (m, 1H,aromatic), 8.71 (m, 1H, aromatic).

EXAMPLE 17

Synthesis of 2-dimethoxymethyl-2-methyl-4-(3'-pyridyl)-2H-1-benzopyran

Step 1) Synthesis of 2-dimethoxymethyl-2-methyl-4-(O-triflate)-6-nitro-2H-1-benzopyran In a dried flask, 2.8 ml of (19.5 mmole) of diisopropylamine was dissolved in 20 ml of distilled THF and 6 ml of dimethoxyethane. To the resultant solution was slowly added 7.8ml (19.5 mmole) of 2.5M solution of n-butyl lithium dissolved in hexane at −78° C. The resultant mixture was stirred for 10 minutes. A solution of 4.02 g (13.0 mmole) of 2-dimethoxymethyl-2-methyl-4-oxo-6-nitro-3,4-dihydro-2H-1-benzopyran obtained in step 2 of Example 10 dissolved in 20 ml of dimethoxyethane was slowly added thereto. The resultant mixture was slowly warmed up to 0° C. and stirred for 1 hour. A solution of 5.57 g (15.6 mmole) of N-phenyl trifluoromethane sulfonimde dissolved in 2 ml of dimethoxyethane was slowly added thereto, which was stirred for 6 hours at 0° C. The resultant mixture was diluted with 100 ml of ethyl acetate and washed with 30 ml of saturated sodium chloride solution. The organic layer was dried over anhydrous magnesium sulfate, evaporated to remove the solvent and purified by silica gel column chromatography using a mixture of hexane and ethyl acetate (4:1) as an eluent to obtain 4.29 g (9.73 mmole, yield 75%) of the title compound.

Step 2) Synthesis of 2-dimethoxymethyl-2-methyl-4-(3'-pyridyl)-6-nitro-2H-1-benzopyran In 2-neck round bottom flask 407 mg (9.68 mmole) of anhydrous lithium chloride was dried sufficiently; and, 62 mg (0.06 mmole) of $Pd_2$ (dba)$_3$ ($CHCl_3$) and 63 mg (0.24 mmole) of triphenylphosphine were added thereto. The reactants were dissolved in 20 ml of THF. Subsequently, a solution of 500 mg (1.21 mmole) of the triflate compound obtained in step 1 and 535 mg (1.45 mmole) of tributyl (3-pyridyl)tin dissolved in THF was added thereto. The resultant solution was heated to reflux for 24 hours, cooled to room temperature and extracted with ethyl acetate. The organic layer was dried over anhydrous $Na_2SO_4$, concentrated and purified by silica gel column chromatography using a mixture of hexane and ethyl aceate (2:1) as an eluent to obtain 150 mg (yield 60%) of the desired compound.

$^1$H NMR (CDCl$_3$) δ1.55 (s, 6H, CH$_3$), 3.55 (d, 6H, (OCH$_3$)$_2$), 4.32 (s, 1H, CH(OCH$_3$)$_2$), 5.85 (s, 1H, H-3), 7.05 (m, 1H,aromatic), 7.4 (m, 1H, aromatic), 7.7 (m, 1H, aromatic), 7.35 (d, 1H,aromatic), 8.1 (dd, 1H, aromatic), 8.7 (m, 2H, aromatic).

EXAMPLE 18

Synthesis of 2-dimethoxymethyl-2-methyl-4-(3'-N-oxopyridyl)-6-nitro-2H-1-benzopyran To a solution of 100 mg (0.29 mmole) of the compound obtained in Example 17 above dissolved in a mixture of 2 ml of acetone and 2 ml of distilled water was added 243 mg (2.9 mmole) of NaHCO$_3$. After stirring the resulting mixture for 10 minutes, 178 mg (0.29 mmole) of oxon was slowly added at room temperature thereto. The resultant solution was stirred for 1 hour and extracted with ethyl acetate. The organic layer was dried over anhydrous Na$_2$SO$_4$, concentrated and purified by silica gel column chromatography using a mixture of methanol and dichloromethane (3:97) as an eluent to obtain 63 mg (yield 61%) of the desired compound as an ivory solid.

$^1$H NMR(CDCl$_3$) δ1.5 (s, 3H, CH$_3$), 3.55 (d, 6H, (OCH$_3$)$_2$), 4.3 (s, 1H, CH(OCH$_3$)$_2$), 5.9 (s, 1H, H-3), 7.0 (d, 1H, aromatic), 7.4 (m, 2H, aromatic), 7.85 (d, 1H, aromatic)) 8. 15 (dd, 1H, aromatic), 8.3 (m, 2H, aromatic).

EXAMPLE 19

Synthesis of 2-dimethoxymethyl-2-methyl-4-(3'-pyridyl)-6-cyano-2H-1-benzopyran

Step 1) Synthesis of 2-dimethoxymethyl-2-methyl-4-(O-triflate)-6-cyano-2H-1-benzopyran Similarly to the procedures described in step 1 of Example 18, the title compound was prepared using the compound obtained in step 1 of Example 11 above.

Step 2) Synthesis of 2-dimethoxymethyl-2-methyl-4-(3'-pyridyl)-6-cyano-2H-1-benzopyran 0.74 g (17.6 mmole) of anhydrous lithium chloride was dried sufficiently; and, 45 mg (0.044 mmole) of Pd$_2$ (dba)$_3$ (CHCl$_3$) and 47 mg (0.18 mmole) of triphenylphosphine were added thereto. To the resultant mixture was added 10 ml of distilled tetrahydrofuran under argon atmosphere. Subsequently, a solution of 0.86 g (2.20 mmole) of the triflate compound obtained in step 1 dissolved in 5 ml of distilled tetrahydrofuran and a solution of 0.98 g (2.66 mmole) of tributyl (3-pyridyl)tin dissolved in 5 ml of distilled tetrahydrofuran were added in turn thereto. The resultant solution was heated to reflux for 40 hours, cooled and extracted with 30 ml of ethyl acetate. The organic layer was dried over anhydrous Na$_2$SO$_4$, concentrated and purified by silica gel column chromatography using a mixture of hexane and ethyl aceate (1:1) as an eluent to obtain 0.46 g (1.43 mmole, yield 65%) of the desired compound.

$^1$H NMR (CDCl$_3$) δ1.50 (s, 3H, CH$_3$), 3.50 (s, 3H, CH(OCH$_3$)$_2$), 3.53 (s, 3H, CH(OCH$_3$)$_2$), 4.30 (s, 1H, CH(OCH$_3$)$_2$), 5.80 (s, 1H, H-3), 6.95 (d, 1H,aromatic), 7.20 (d, 1H, aromatic), 7.40 (m, 2H, aromatic), 7.65 (m, 1H, aromatic), 8.58 (d, 1H, aromatic), 8.65 (dd, 1H, aromatic).

EXAMPLE 20

Synthesis of 2-dimethoxymethyl-2-methyl-4-(3'-N-oxopyridyl)-6-cyano-2H-1-benzopyran Similarly to the procedures described in Example 10 above, 0.11 g (0.33 mmole, yield 70%) of the desired compound was prepared using 0.15 g (0.47 mmole) of the compound obtained in Example 19 above, 0.40 g (4.70 mmole) of NaHCO$_3$ and 0.29(0.47 mmole) of oxon.

$^1$H NMR (CDCl$_3$) δ1.50 (s, 3H, CH$_3$), 3.48 (s, 3H, CH(OCH$_3$)$_2$), 3.55 (s, 3H, CH(OCH$_3$)$_2$), 4.28 (s, 1H, CH(OCH$_3$)$_2$), 5.87 (s, 1H, H-3), 6.95 (d, 1H,aromatic), 7.20 (d, 1H,aromatic), 7.22 (m, 2H, aromatic ), 7.38 (t, 1H, aromatic), 7.49 (dd, 1H, aromatic ), 8.27 (m, 2H,aromatic).

EXAMPLE 21

Synthesis of 2-(2''-(1'',3''-dioxolane))-2-methyl-4-(3'-N-oxopyridyl)-6-nitro-2H-1-benzopyran To a solution of 171 mg (0.48 mmole) of 2-dimethoxymethyl-2-methyl-4-(3'-N-oxopyridyl)-6-nitro-2H-1-benzopyran obtained in Example 18 above dissolved in 20 mg of toluene were added 100 mg (2.4 mmole) of ethylene glycol and 11.4 mg (0.06 mmole) of p-toluene sulfonic acid. The reaction mixture was heated to reflux for 3 hours with Dean-Stark apparatus. The reaction mixture was cooled to room temperature after completion of the reaction, diluted with 20 ml of ethyl acetate, washed with 10 mg of a saturated NaHCO$_3$ solution and then 10 ml of saturated sodium chloride solution, dried over anhydrous MgSO$_4$, filtered and concentrated under reduced pressure. The residue obtained was purified by silica gel column chromatography using a mixture of hexane and ethyl acetate (1:1) as an eluent to obtain 145 mg (0.41 mmole, yield 85%) of the desired compound as a white solid.

$^1$H NMR (CDCl$_3$, 200 MHz) δ1.57 (s, 3H), 4.01 (m, 4H), 5.06 (s, 1H), 5.89 (s, 1H), 6.93 (m, 2H), 7.40 (m, 4H), 8.35 (m, 1H).

EXAMPLE 22

Synthesis of 2-(2''-(1'',3''-dioxolane))-2-methyl-4-(3'-N-oxopyridyl)-6-cyano-2H-1-benzopyran To a solution of 150 mg (0.48 mmole) of 2-dimethoxymethyl-2-methyl-4-(3'-N-oxopyridyl)-6-cyano-2H-1- benzopyran obtained in Example 20 above dissolved in 20 ml of toluene were added 100 mg (2.4 mmole) of ethylene glycol and 11.4 mg (0.06 mmole) of p-toluene sulfonic acid. The reaction mixture was heated to reflux for 3 hours with Dean-Stark apparatus. The reaction mixture was cooled to room temperature after completion of the reaction, diluted with 10 ml of ethyl acetate, washed with 10 ml of a saturated $NaHCO_3$ solution and then 10 ml of saturated sodium chloride solution, dried over anhydrous $MgSO_4$, filtered and concentrated under reduced pressure. The residue so obtained was purified by silica gel column chromatography using a mixture of hexane and ethyl acetate (1:1) as an eluent to obtain 130 mg (0.42 mmole, yield 87%) of the desired compound as a white solid.

$^1H$ NMR ($CDCl_3$, 300 MHz) $\delta$1.57 (s, 3H), 4.01 (m, 4H), 5.06 (s, 1H), 5.89 (s, 1H), 6.93 (m, 2H), 7.40 (m, 4H), 8.35 (m, 1H).

EXAMPLE 23

Synthesis of
2-(2″-(1″,3″-dioxolane))-2-methyl-4-(3′-pyridyl)-6-nitro-2H-1-benzopyran Similarly to the procedures described in Example 21 and 22 above, the desired compound was prepared using the compound obtained in Example 17 above.

$^1H$ NMR ($CDCl_3$, 300 MHz)$\delta$ 1.56 (s, 3H, $C(CH_3)_2$), 3.90 (m, 2H, $OCH_2CH_2$), 4.08 (m, 2H, $OCH_2CH_2$), 4.38 (s, 1H, $CH(OCH_2)_2$), 5.99 (s, 1H, H-3), 6.98 (m, 1H, aromatic 7.42 (m, 4H, aromatic 8.30 (dd, 1H, aromatic).

EXAMPLE 24

Synthesis of
2-(2″-(1″,3″-dioxolane))-2-methyl-4-(3′-pyridyl)-6-cyano-2H-1-benzopyran Similarly to the procedures described in Example 21 and 22 above, the desired compound was prepared using the compound obtained in Example 19 above.

$^1H$ NMR ($CDCl_3$, 300 MHz)$\delta$ 1.54 (s, 3H, $C(CH_3)_2$), 3.89 (m, 2H, $OCH_2CH_2$), 4.06 (m, 2H, $OCH_2CH_2$), 4.39 (s, 1H, $CH(OCH_2)_2$), 5.97 (s, 1H, H-3), 6.95 (m, 2H, aromatic ), 7.40 (m, 4H, aromatic), 8.35 (dd, 1H, aromatic).

EXAMPLE 25

Synthesis of
2-(2″-(1″,3″-dioxane))-2-methyl-4-(3′-N-oxopyridyl)-6-nitro-2H-1-benzopyran Similarly to the procedures described in Example 21 and 22 above, the desired compound was prepared using the compound obtained in Example 18 above.

$^1H$ NMR ($CDCl_3$, 300 MHz)$\delta$ 1.35 (m, 2H, $OCH_2CH_2CH_2$), 1.56 (s, 3H, $C(CH_3)_2$), 3.83 (m, 2H, $OCH_2CH_2CH_2$), 4.20 (m, 2H, $OCH_2CH_2CH_2$), 4.38 (s, 1H, $CH(OCH_2)_2CH_2$), 5.99 (s, 1H, H-3), 6.93 (m, 2H, aromatic 7.45 (m, 4H, aromatic ), 8.30 (dd, 1H, aromatic).

EXAMPLE 26

Synthesis of
2-(2″-(1″,3″-dioxane))-2-methyl-4-(3′-N-oxopyridyl)-6-cyano-2H-1-benzopyran Similarly to the procedures described in Example 25 above, the desired compound was prepared using the compound obtained in Example 20 above.

$^1H$ NMR ($CDCl_3$, 300 MHz)$\delta$ 1.33 (m, 2H, $OCH_2CH_2CH_2$), 1.56 (s, 3H, $C(CH_3)_2$), 3.82 (m, 2H, $OCH_2CH_2CH_2$), 4.21(m, 2H, $OCH_2CH_2CH_2$), 4.38 (s, 1H, $CH(OCH_2)_2CH_2$), 5.98(s, 1H, H-3), 6.94 (m, 2H, aromatic).

EXAMPLE 27

Synthesis of
2-(2″-(1″,3″-dioxane))-2-methyl-4-(3′-pyridyl)-6-nitro-2H-1-benzopyran Similarly to the procedures described in Example 25 above, the desired compound was prepared using the compound obtained in Example 17 above.

$^1H$ NMR ($CDCl_3$, 300 MHz)$\delta$ 1.35 (m, 2H, $OCH_2CH_2CH_2$), 1.53 (s, 3H, $C(CH_3)_2$), 3.83 (m, 2H, $OCH_2CH_2CH_2$), 4.21 (m, 2H, $OCH_2CH_2CH_2$), 4.33 (s, 1H, $CH(OCH_2)_2CH_2$), 6.05 (s, 1H, H-3), 6.95 (d, 1H, aromatic ), 7.33 (m, 1H, aromatic ), 7.48 (dd, 1H, aromatic ), 7.80 (t, 1H, aromatic ), 8.07 (dd, 1H, aromatic), 8.29 (dd, 1H, aromatic ), 8.72 (dd, 5H, aromatic).

EXAMPLE 28

Synthesis of
2-(2″-(1″,3″-dioxane))-2-methyl-4-(3′-pyridyl)-6-cyano-2H-1-benzopyran Similarly to the procedures described in Example 25 above, the desired compound was prepared using the compound obtained in Example 19 above.

$^1H$ NMR ($CDCl_3$, 300 MHz)$\delta$ 1.32 (m, 2H, $OCH_2CH_2CH_2$), 1.50 (s, 3H, $C(CH_3)_2$), 3.82(m, 2H, $OCH_2CH_2CH_2$), 4.20 (m, 2H, $OCH_2CH_2CH2$), 4.33 (s, 1H, $CH(OCH_2)_2CH_2$), 6.02 (s, 1H, H-3), 6.9(d, 1H, aromatic), 7.24~7.82 (m, 5H, aromatic ), 8.70 (dd, 1H, aromatic).

EXAMPLE 29

Synthesis of
2-(2″-(1″,3″-dioxolane))-2-methyl-4-(2′-N-oxopyridyl)-6-nitro-2H-1-benzopyran Similarly to the procedures described in Example 21 and 22 above, the desired compound was prepared using the compound obtained in Example 10 above.

$^1H$ NMR ($CDCl_3$, 300 MHZ)$\delta$1.56 (s, 3H), 3.90 (m, 2H), 4.10 (m, 2H), 4.38 (s, 1H), 5.96 (s, 1H), 6.93 (m, 2H), 7.40 (m, 4H), 8.30 (dd, 1H).

EXAMPLE 30

Synthesis of
2-(2″-(1″,3″-dioxolane))-2-methyl-4-(2′-pyridyl)-6-nitro-2H-1-benzopyran Similarly to the procedures described in Example 21 and 22 above, the desired compound was prepared using the compound obtained in Example 9 above.

$^1H$ NMR ($CDCl_3$, 300 MHz)$\delta$1.56 (s, 3H, $C(CH_3)_2$), 3.90 (m, 2H, $OCH_2CH_2$), 4.08 (m, 2H, $OCH_2CH_2$), 4.38(s, 1H, $CH(OCH_2)_2$), 5.99 (s, 1H, H-3), 6.98 (m, 1H, aromatic),7.42 (m, 4H, aromatic), 8.30 (dd, 1H, aromatic).

EXAMPLE 31

Synthesis of
2-(2″-(1″,3″-dioxolane))-2-methyl-4-(2′-N-oxopyridyl)-6-cyano-2H-1-benzopyran Similarly to the procedures described in Example 21 and 22 above, the desired compound was prepared using the compound obtained in Example 12 above.

¹H NMR (CDCl₃, 300 MHz)δ1.57 (s, 3H), 4.01 (m, 4H), 5.06 (s, 1H), 5.89 (s, 1H), 6.93 (m, 2H), 7.40 (m, 4H), 8.35 (m, 1H).

EXAMPLE 32

Synthesis of 2-(2''-(1'',3''-dioxolane))-2-methyl-4-(2'-pyridyl)-6-cyano-2H-1-benzopyran Similarly to the procedures described in Example 21 and 22 above, the desired compound was prepared using the compound obtained in Example 11 above.

¹H NMR (CDCl₃, 300 MHz) δ1.54 (s, 3H, C(CH₃)₂)), 3.89 (m, 2H, OCH₂CH₂), 4.06 (m, 2H, OCH₂CH₂), 4.39 (s, 1H, CH(OCH₂)₂), 5.97 (s, 1H, H-3), 6.95 (m, 2H, aromatic), 7.40 (m, 4H, aromatic), 8.35 (dd, 1H, aromatic).

EXAMPLE 33

Synthesis of 2-(2''-(1'',3''-dioxane))-2-methyl-4-(2'-N-oxopyridyl)-6-nitro-2H-1-benzopyran Similarly to the procedures described in Example 25 above, the desired compound was prepared using the compound obtained in Example 10 above.

¹H NMR (CDCl₃, 300 MHz)δ1.35 (m, 2H, OCH₂CH₂CH₂), 1.56(s, 3H, C(CH₃)₂), 3.83 (m, 2H, OCH₂CH₂CH₂), 4.20 (m, 2H, OCH₂CH₂CH₂), 4.38 (s, 1H, CH(OCH₂)₂CH₂), 5.99 (s, 1H, H-3), 6.93 (m, 2H, aromatic), 7.45 (m, 4H, aromatic), 8.30 (dd, 1H, aromatic).

EXAMPLE 34

Synthesis of 2-(2''-(1'',3''-dioxane))-2-methyl-4-(2'-pyridyl)-6-nitro-2H-1-benzopyran Similarly to the procedures described in Example 25 above, the desired compound was prepared using the compound obtained in Example 9 above.

¹H NMR (CDCl₃, 300 MHz)δ1.35 (m, 2H, OCH₂CH₂CH₂), 1.63 (s, 3H, C(CH₃)₂), 3.83 (m, 2H, OCH₂CH₂CH₂), 4.21 (m, 2H, OCH₂CH₂CH₂), 4.33 (s, 1H, CH(OCH₂)₂CH₂), 6.05 (s, 1H, H-3), 6.95 (d, 1H, aromatic),7.33 (m, 1H, aromatic),7.48 (d, 1H, aromatic), 7.80 (t, 1H, aromatic), 8.07 (dd, 1H, aromatic), 8.29 (dd, 1H, aromatic), 8.72 (dd, 5H, aromatic).

EXAMPLE 35

Synthesis of 2-(2''-(1'',3''-dioxane))-2-methyl-4-(2'-N-oxopyridyl)-6-cyano-2H-1-benzopyran Similarly to the procedures described in Example 25 above, the desired compound was prepared using the compound obtained in Example 12 above.

¹H NMR (CDCl₃, 300 MHz)δ1.33 (m, 2H, OCH₂CH₂CH₂), 1.56 (s, 3H, C(CH₃)₂), 3.82 (m, 2H, OCH₂CH₂CH₂), 4.21 (m, 2H), OCH₂CH₂CH₂), 4.38 (s, 1H, CH(OCH₂)₂CH₂), 5.93 (s, 1H, H-3), 6.94 (m, 2H, aromatic),7.40 (m, 4H, aromatic),8.35 (dd, 1H, aromatic).

EXAMPLE 36

Synthesis of 2-(2''-(1'',3''-dioxane))-2-methyl-4-(2'-pyridyl)-6-cyano-2H-1-benzopyran Similarly to the procedures described in Example 25 above, the desired compound was prepared using the compound obtained in Example 11 above.

¹NMR (CDCl₃, 300 MHz)δ1.32 (m, 2H, OCH₂CH₂CH₂), 1.50 (s, 3H, C(CH₃)₂), 3.82 (m, 2H, OCH₂CH₂CH₂), 4.20 (m, 2H, OCH₂CH₂CH₂), 4.33 (s, 1H, CH(OCH₂)₂CH₂), 6.02 (s, 1H, H-3), 6.92 (d, 1H, aromatic),7.24~7.32 (m, 6H,aromatic),8.70 (dd, 1H,aromatic).

Activity Test

The activity of the formula (I) compounds of the present invention was tested by employing the tail-cuff method described in references [see, e.g., I. M. Claxton, M. G. Palfreyman, R. H. Poyster a-nd R. L. Whiting, *European Journal of Phalmacology* 37, 179 (1976)]. After administration of the test compounds of formula (I) to sets of spontaneously hypertensive rats, maximum blood pressure-lowering activity was determined by measuring the lowering effect on systolic blood pressure. The results of the test are shown in Table 1.

Further, the relaxation activity on respiratory smooth muscle was determined as follows: Guinea pig trachea muscle was made to be contracted with histamine; and, then, the test compounds of the present invention were administered thereto; and the concentration of the test compounds which was required in relaxing 50% level of the contraction was designated as EC₅₀. These EC₅₀ values for the test compounds are also shown in Table 1.

TABLE 1

| Example No. of Compound Employed | Trachea Relaxation Activity, EC₅₀ | Blood Pressure-Lowering Activity (%, dose) |
|---|---|---|
| 2 | $2.23 \times 10^{-6}$ M | 40 (0.1 mg) |
| 4 | $4.0 \times 10^{-6}$ M | 10.5 (0.5 mg) |
| 6 | $1.1 \times 10^{-6}$ M | 15 (0.1 mg) |
| 8 | $2.64 \times 10^{-5}$ M | 22 (0.5 mg) |
| 10 | $1.23 \times 10^{-6}$ M | 30.4 (0.03 mg) |
| 12 | $5.0 \times 10^{-6}$ M | 48.1 (0.03 mg) |
| 14 | $1.71 \times 10^{-5}$ M | 20 (0.1 mg) |
| 18 | $5.12 \times 10^{-5}$ M | 36 (0.1 mg) |
| 20 | $3.98 \times 10^{-5}$ M | 20 (1 mg) |
| 26 | $5.12 \times 10^{-5}$ M | 35.5 (1 mg) |
| 32 | $9.77 \times 10^{-7}$ M | 51 (0.03 mg) |
| 36 | $3.23 \times 10^{-6}$ M | 40 (0.03 mg) |
| Cromakalim⁽⁻⁾* | $2.7 \times 10^{-6}$ M | 39 (0.3 mg) |

*represents isomeric form.

Toxicity Test

The toxicity test of the formula (1) compounds was conducted as follows:

The compounds prepared in Examples 1 and 11 were orally administered to sets of rats, which had a body weight of 100-120 g and were about four week-old. Six pairs (each pair consisting of a male and a female) of the rats were used in the test. The number of the rats which died over a period of 48 hours was reported. The results of the test are shown in Table 2.

TABLE 2

| Example No. of Compound Employed | Dose (mg/kg) | Lethal Rate | LD$_{50}$* |
|---|---|---|---|
| 10 | 10 | 0 | >50 mg/kg |
|  | 20 | 15 |  |
|  | 50 | 35 |  |
| 30 | 10 | 0 | >50 mg/kg |
|  | 20 | 12.5 |  |
|  | 50 | 25 |  |

*LD$_{50}$ (lethal dose) represents the amount of a test compound which causes a 50% lethal rate As shown above, the compounds of the present invention are judged to be safe for use, especially at the amount to be administered.

We claim:

1. A novel benzopyran compound of formula(I)

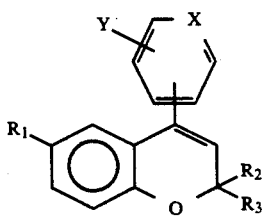

wherein:

$R_1$ is —CN, —NO$_2$, —OCX$_1$X$_2$X$_3$, —NH$_2$, 'NHSO$_2$R$^A$,

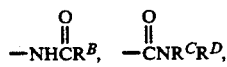

—SO$_2$R$^C$ or —SO$_2$NR$^C$R$^D$ wherein X$_1$, X$_2$ and X$_3$ are, each independently, F, Cl or H, except that X$_1$, X$_2$ and X$_3$ may not be a hydrogen atom, simultaneously; R$^A$ and R$^B$ are, each independently, a hydrogen atom, a C$_{1-6}$ alkyl group, an optionally substituted phenyl group with a halogen atom, or a straight or branched C$_{1-3}$ alkyl group; and R$^C$ and R$^D$ are, each independently, a hydrogen atom, a C$_{1-6}$ alkyl group, an optionally substituted phenyl group with a halogen atom, or a straight or branched C alkyl group;

R$_2$ is a C$_{1-4}$ straight or branched alkyl group;

R$_3$ is

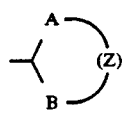

wherein A and B are, each independently, S or O; and Z is a C$_{1-3}$ straight or branched alkyl group;

X is N or N→O; and

Y is a hydrogen or halogen atom, or an amino, hydroxy, lower alkoxy or lower alkyl group.

2. The compound of claim 1 wherein:

R$_1$ is —CN or —NO$_2$;

R$_2$ is a methyl group;

R$_3$ is

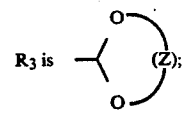

X is N→O, and
Y is H.

3. The compound of claim 2 wherein:

R$_1$ is —CN or —NO$_2$;

R$_2$ is a methyl group;

R$_3$ is

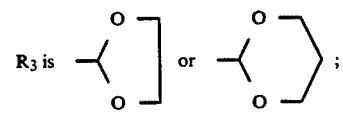

X is N→O, and
Y is H.

4. The compound of claim 1 which is selected from the group consisting of:

2,2-dimethyl-4-(3'-N-oxopyridyl)-6-nitro-2H-1-benzopyran;
2,2-dimethyl-4-(4'-N-oxopyridyl)-6-nitro-2H-1-benzopyran;
2-dimethoxymethyl-2-methyl-4-(2'-N-oxopyridyl)-6-nitro-2H-1-benzopyran;
2-dimethoxymethyl-2-methyl-4-(4'-N-oxopyridyl)-6-nitro-2H-1-benzopyran;
2-dimethoxymethyl-2-methyl-4-(2'-N-oxopyridyl)-6-cyano-2H-1-benzopyran;
2-dimethoxymethyl-2-methyl-4-(2'-N-oxopyridyl)-6-trifluoromethoxy-2H-1-benzopyran;
2-dimethoxymethyl-2-methyl-4-(3'-N-oxopyridyl)-6-nitro-2H-1-benzopyran;
2-dimethoxymethyl-2-methyl-4-(3'-N-oxopyridyl)-6-cyano-2H-1-benzopyran;
2-(2''-(1'',3''-dioxolane))-2-methyl-4-(3'-N-oxopyridyl)-6-nitro-2H-1-benzopyran;
2-(2''-(1'',3''-dioxolane))-2-methyl-4-(3'-N-oxopyridyl)-6-cyano-2H-1-benzopyran;
2-(2''-(1'',3''-dioxolane))-2-methyl-4-(2'-N-oxopyridyl)-6-nitro-2H-1-benzopyran;
2-(2''-(1'',3''-dioxolane))-2-methyl-4-(2'-N-oxopyridyl)-6-cyano-2H-1-benzopyran; and
2-(2''-(1'',3''-dioxolane))-2-methyl-4-(4'-N-oxopyridyl)-6-nitro-2H-1-benzopyran.

5. A pharmaceutical composition comprising an effective amount of a compound of formula (I) defined in claim 1 as an active ingredient, and a pharmaceutically acceptable carrier.

* * * * *